United States Patent
Garibyan et al.

(10) Patent No.: US 11,564,830 B2
(45) Date of Patent: Jan. 31, 2023

(54) MEDICAL ICE SLURRY PRODUCTION AND DELIVERY SYSTEMS AND METHODS

(71) Applicant: The General Hospital Corporation, Boston, MA (US)

(72) Inventors: Lilit Garibyan, Brookline, MA (US); Richard Rox Anderson, Boston, MA (US); William A. Farinelli, Danvers, MA (US); Emilia Javorsky, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 593 days.

(21) Appl. No.: 16/080,092

(22) PCT Filed: Feb. 24, 2017

(86) PCT No.: PCT/US2017/019268
§ 371 (c)(1),
(2) Date: Aug. 27, 2018

(87) PCT Pub. No.: WO2017/147367
PCT Pub. Date: Aug. 31, 2017

(65) Prior Publication Data
US 2019/0053939 A1 Feb. 21, 2019

Related U.S. Application Data

(60) Provisional application No. 62/300,679, filed on Feb. 26, 2016.

(51) Int. Cl.
*A61F 7/00* (2006.01)
*A61B 18/02* (2006.01)
(Continued)

(52) U.S. Cl.
CPC .......... *A61F 7/0085* (2013.01); *A61M 5/158* (2013.01); *F25C 1/12* (2013.01);
(Continued)

(58) Field of Classification Search
CPC ............ A61F 7/0085; A61F 2007/0063; A61F 2007/0288; A61M 5/158; A61M 5/142;
(Continued)

(56) References Cited

U.S. PATENT DOCUMENTS

| 4,883,665 A | 11/1989 | Miyazima et al. |
| 4,986,079 A | 1/1991 | Koseki et al. |

(Continued)

FOREIGN PATENT DOCUMENTS

| CN | 204468406 U | 7/2015 |
| CN | 105640642 A | 6/2016 |

(Continued)

OTHER PUBLICATIONS

European Patent Office, Extended European Search Report, Application No. 17757262.5, dated Aug. 26, 2019, 14 pages.

(Continued)

*Primary Examiner* — Khadijeh A Vahdat
(74) *Attorney, Agent, or Firm* — Wolf, Greenfield & Sacks, P.C.

(57) ABSTRACT

The present disclosure provides systems and method for medical ice slurry production. In particular, systems and methods are provided for medical ice slurry production that enable an end user to produce and deliver a sterile medical ice slurry at the point of care.

20 Claims, 27 Drawing Sheets

(51) Int. Cl.
  *F25C 1/12* (2006.01)
  *A61M 5/158* (2006.01)
  *A61M 5/142* (2006.01)

(52) U.S. Cl.
  CPC ...... *A61F 2007/0063* (2013.01); *A61M 5/142* (2013.01); *F25C 2301/002* (2013.01); *F25C 2400/00* (2013.01)

(58) Field of Classification Search
  CPC ............ A61M 5/44; A61M 2005/3128; A61M 2205/3606; F25C 1/12; F25C 2400/00; F25C 2301/002; A61B 18/02; A61B 2018/0293; A61J 1/05; A61J 2200/44; A61K 31/047; A61K 47/02; A61K 9/0019; A61K 9/016; B01F 27/00; B01F 33/50112
  USPC ..................................................... 606/21–26
  See application file for complete search history.

(56) References Cited

U.S. PATENT DOCUMENTS

| | | | |
|---|---|---|---|
| 5,005,364 A | 4/1991 | Nelson | |
| 5,143,063 A | 9/1992 | Fellner | |
| 5,507,790 A | 4/1996 | Weiss | |
| 5,769,879 A | 6/1998 | Richards et al. | |
| 6,126,684 A | 10/2000 | Boyden et al. | |
| 6,244,052 B1 | 6/2001 | Kasza | |
| 6,413,444 B1* | 7/2002 | Kasza | A61F 7/12 252/70 |
| 6,430,957 B1 | 8/2002 | Inada et al. | |
| 6,962,601 B2 | 11/2005 | Becker et al. | |
| 7,367,341 B2 | 5/2008 | Anderson et al. | |
| 7,422,601 B2 | 9/2008 | Becker et al. | |
| 7,507,234 B2 | 3/2009 | Utley et al. | |
| 7,897,141 B2 | 3/2011 | Wheatley et al. | |
| 8,505,315 B2 | 8/2013 | Kasza et al. | |
| 8,715,622 B2 | 5/2014 | Wheatley et al. | |
| 8,840,608 B2 | 9/2014 | Anderson et al. | |
| 9,980,076 B1 | 5/2018 | Avram et al. | |
| 10,582,960 B2 | 3/2020 | Avram et al. | |
| 2002/0021741 A1 | 2/2002 | Faries et al. | |
| 2002/0107199 A1 | 8/2002 | Walker | |
| 2003/0032996 A1 | 2/2003 | Hallman | |
| 2003/0181897 A1 | 9/2003 | Thomas et al. | |
| 2004/0068309 A1 | 4/2004 | Edelman | |
| 2004/0176755 A1 | 9/2004 | Lafontaine | |
| 2004/0210212 A1 | 10/2004 | Maurice et al. | |
| 2004/0215295 A1 | 10/2004 | Littrup et al. | |
| 2005/0123666 A1 | 6/2005 | Vaghela et al. | |
| 2005/0203598 A1 | 9/2005 | Becker et al. | |
| 2005/0251120 A1 | 11/2005 | Anderson et al. | |
| 2006/0079869 A1 | 4/2006 | Bischof et al. | |
| 2006/0161232 A1 | 7/2006 | Kasza et al. | |
| 2006/0235375 A1 | 10/2006 | Littrup et al. | |
| 2007/0010861 A1 | 1/2007 | Anderson et al. | |
| 2007/0056313 A1* | 3/2007 | Kasza | A61F 7/0085 62/353 |
| 2007/0106247 A1 | 5/2007 | Burnett et al. | |
| 2008/0183164 A1 | 7/2008 | Elkins et al. | |
| 2008/0236186 A1 | 10/2008 | Kasza et al. | |
| 2008/0247957 A1 | 10/2008 | Wheatley | |
| 2008/0279783 A1 | 11/2008 | Wheatley et al. | |
| 2008/0300571 A1 | 12/2008 | Lepivert | |
| 2009/0028797 A1 | 1/2009 | Wheatley et al. | |
| 2009/0118722 A1 | 5/2009 | Ebbers et al. | |
| 2009/0234325 A1 | 9/2009 | Rozenberg et al. | |
| 2009/0255276 A1* | 10/2009 | Kasza | F25C 1/00 62/68 |
| 2009/0301107 A1* | 12/2009 | Kammer | B01F 11/0002 62/68 |
| 2009/0326621 A1* | 12/2009 | El-Galley | A61F 7/12 607/105 |
| 2010/0036295 A1 | 2/2010 | Altshuler et al. | |
| 2010/0113615 A1 | 5/2010 | Boyden et al. | |
| 2010/0137304 A1 | 6/2010 | Gilday et al. | |
| 2010/0152880 A1 | 6/2010 | Boyden et al. | |
| 2010/0179527 A1 | 7/2010 | Watson et al. | |
| 2011/0009748 A1 | 1/2011 | Greene et al. | |
| 2012/0323232 A1 | 12/2012 | Wolf et al. | |
| 2013/0011332 A1 | 1/2013 | Boyden et al. | |
| 2013/0184695 A1 | 7/2013 | Fourkas et al. | |
| 2013/0190744 A1 | 7/2013 | Avram et al. | |
| 2013/0324989 A1 | 12/2013 | Leung et al. | |
| 2014/0200511 A1 | 7/2014 | Boyden et al. | |
| 2014/0303697 A1 | 10/2014 | Anderson et al. | |
| 2016/0151200 A1 | 6/2016 | Kammer et al. | |
| 2016/0175141 A1* | 6/2016 | Wu | A61F 7/0085 607/105 |
| 2017/0274011 A1 | 9/2017 | Garibyan et al. | |
| 2017/0274078 A1 | 9/2017 | Garibyan et al. | |
| 2018/0250056 A1 | 9/2018 | Avram et al. | |
| 2019/0183558 A1 | 6/2019 | Anderson et al. | |
| 2019/0192424 A1 | 6/2019 | Garibyan et al. | |
| 2021/0236639 A1 | 8/2021 | Garibyan et al. | |
| 2021/0244817 A1 | 8/2021 | Garibyan et al. | |
| 2022/0079874 A1 | 3/2022 | Garibyan et al. | |

FOREIGN PATENT DOCUMENTS

| | | |
|---|---|---|
| EP | 2561886 A1 | 2/2013 |
| JP | 2003-534366 A | 11/2003 |
| JP | 06-510758 A | 3/2006 |
| JP | 2010-508130 A | 3/2010 |
| JP | 2011-516168 A | 5/2011 |
| JP | 2017-526684 A | 9/2017 |
| WO | WO 90/03795 A | 4/1990 |
| WO | 9300930 A1 | 1/1993 |
| WO | WO 2001/05372 A2 | 1/2001 |
| WO | 0191720 A2 | 12/2001 |
| WO | WO 2003/078596 A2 | 9/2003 |
| WO | WO 2008/015380 A2 | 2/2008 |
| WO | WO 2008/055243 A2 | 5/2008 |
| WO | 2009009540 A1 | 1/2009 |
| WO | WO 2009/047362 A2 | 4/2009 |
| WO | WO 2009/102367 A2 | 8/2009 |
| WO | WO 2009/146053 A1 | 12/2009 |
| WO | WO 2011/100692 A1 | 8/2011 |
| WO | WO 2013/059133 A1 | 4/2013 |
| WO | 2015019257 A1 | 2/2015 |
| WO | WO 2016/033380 A1 | 3/2016 |
| WO | WO 2016/033384 A1 | 3/2016 |
| WO | WO 2017/147367 A1 | 8/2017 |
| WO | WO 2018/044825 A1 | 3/2018 |
| WO | WO 2021/151019 A1 | 7/2021 |

OTHER PUBLICATIONS

Barnard, The Effects of Extreme Cold on Sensory Nerves, Annals of the Royal College of Surgeons of England, 1980, 62:180-187.

Calandria, Cryoanalgesia for Post-Herpetic Neuralgia: A New Treatment, International Journal of Dermatology, 2011, 50(6):746-750.

Conaway, Ice Packs in Diabetic Neuropathy, Physical Therapy Review, 1961, 41(8):586-588.

Fruhstorfer, et al., The Effects of Thermal Stimulation on Clinical and Experimental Itch, Pain, 1986, 24(2):259-269.

Garbay, et al., Myelin Synthesis in the Peripheral Nervous System, Progress in Neurobiology, 2000, 61:267-304.

Ge, et al., Estimation of Freezing Point Depression, Boiling Point Elevation, and Vaporization Enthalpies of Electrolyte Solutions, Industrial & Engineering Chemistry Research, 2009, 48(4):2229-2235.

Ge, et al., Calculations of Freezing Point Depression, Boiling Point Elevation, Vapor Pressure and Enthalpies of Vaporization of Electrolyte Solutions by a Modified Three-Characteristic Parameter Correlation Model, Journal of Solution Chemistry, 2009, 38(9):1097-1117.

Halkier-Sorensen, et al., The Relevance of Low Skin Temperature Inhibiting Histamine-Induced Itch to the Location of Contact Urticarial

(56) References Cited

OTHER PUBLICATIONS

Symptoms in the Fish Processing Industry, Contact Dermatitis, 1989, 21(3): 179-183.
Han, et al., Efficacy and Safety of High Concentration Lidocaine for Trigeminal Nerve Block in Patients with Trigeminal Neuralgia, International Journal of Clinical Practice, 2008, 62(2):248-254 [Abstract Only].
Hargreaves, et al., A New and Sensitive Method for Measuring Thermal Nociception in Cutaneous Hyperalgesia, Pain, 1988, 32:77-88.
Kauffeld, et al., Ice Slurry Applications, Int. J. Refrig., 2010, 33(8):1491-1505.
Lampe, et al., Rapid Induction of Heterogeneous Ice Nucleation in a Biologically Compatible Coolant, International Journal of Transport Phenomena, 2011, 12(3-4):307-317.
Lenz, et al., The Freezing Threshold of the Peripheral Motor Nerve: An Electrophysiological and Light-Microscopical Study on the Sciatic Nerve of the Rabbit, Cryobiology, 1975, 12(5):486-496.
Mitchell, et al., Degeneration of Non-Myelinated Axons in the Rat Sciatic Nerve Following Lysolecithin Injection, Acta Neuropathologica, 1982, 56(3):187-193.
Modak, et al., Agglomeration Control of Ice Particles in Ice-Water Slurry System Using Surfactant Additives, HVAC&R Research, 2002, 8(4):453-466.
Pradel, et al., Cryosurgical Treatment of Genuine Trigeminal Neuralgia, British Journal of Oral and Maxillofacial Surgery, 2002, 40(3):244-247.
Pramanick, et al., Excipient Selection in Parenteral Formulation Development, Pharma Times, 2013, 45(3):65-77.
Shikanov, et al., Microparticulate ICE Slurry for Renal Hypothermia: Laparoscopic Partial Nephrectomy in a Porcine Model, Urology, 2010, 76(4)1012-1016.
Suzuki, et al., Particle Size Depression and Drag Reduction of Ice Slurry Treated with Combination Additives of Surfactants and Poly(vinyl alcohol). Journal of Chemical Engineering of Japan, 2010, 43(6):482-486.
Vanden Hoek, et al., Induced Hypothermia by Central Venous Infusion: Saline Ice Slurry Versus Chilled Saline, Crit Care Med., 2004, 32(9)(Suppl.):S425-S431.
Polysorbate-20 (https://web.archive.org/web/20130315082056/http://www.ewg.org:80/skindeep/ingredient/705137/POLYSORBATE-20) available Mar. 15, 2013, pp. 1-3 (Year: 2013).
Isotonic Definition (https://biologydictionary.net/isotonic/) accessed by examiner in related application on Jun. 21, 2018, pp. 1-4 (Year: 2018).
PCT International Search Report and Written Opinion, PCT/US2017/019268, dated May 15, 2017.
International Search Report and Written Opinion dated Apr. 12, 2011 for Application No. PCT/US2011/024766.
International Preliminary Report on Patentability dated Aug. 30, 2012 for Application No. PCT/US2011/024766.
International Search Report and Written Opinion for International Application No. PCT/US2020/043280 dated Nov. 9, 2020.
International Search Report and Written Opinion for International Application No. PCT/US2015/047292 dated Dec. 7, 2015.
International Preliminary Report on Patentability dated Mar. 9, 2017 for Application No. PCT/US2015/047292.
Partial European Search Report dated Mar. 22, 2018 for Application No. EP 15836780.5.
Extended European Search Report dated Jun. 26, 2018 for Application No. EP 15836780.5.
International Search Report and Written Opinion for International Application No. PCT/US2015/047301 dated Dec. 14, 2015.
International Preliminary Report on Patentability dated Mar. 9, 2017 for Application No. PCT/US2015/047301.
Partial European Search Report dated Mar. 24, 2020, for Application No. EP 17847238.6.
Extended European Search Report dated Dec. 7, 2020 for Application No. EP 17847328.6.
International Search Report and Written Opinion dated Nov. 3, 2017 for Application No. PCT/US2017/048995.
International Preliminary Report on Patentability dated Mar. 14, 2019 for Application No. PCT/US2017/048995.
International Preliminary Report on Patentability dated Sep. 7, 2018 for Application No. PCT/US2017/019268.
Abbott et al., Front. Pharmacol. Conference Abstract: Structure and function of the blood-brain barrier. Pharmacology and Toxicology of the Blood-Brain Barrier: State of the Art, Needs for Future Research and Expected Benefits for the EU. Feb. 11-12, 2010. (doi:10.3389/conf.fphar.2010.02.00002).
Armitage et al., Toxic and osmotic effects of glycerol on human granulocytes. Am J Physiol. Nov. 1984;247(5 Pt 1):C382-9. doi: 10.1152/ajpcell.1984.247.5.C382.
Ash, Chronic peritoneal dialysis catheters: overview of design, placement, and removal procedures. Semin Dial. Jul.-Aug. 2003;16(4):323-34.
Ballabh et al., The blood-brain barrier: an overview: structure, regulation, and clinical implications. Neurobiol Dis. Jun. 2004;16(1):1-13. doi: 10.1016/j.nbd.2003.12.016.
Brink et al., Abdominoplasty with direct resection of deep fat. Plast Reconstr Surg. May 2009;123(5):1597-603. doi: 10.1097/PRS.0b013e3181a07708.
Ding et al., Association between non-subcutaneous adiposity and calcified coronary plaque: a substudy of the Multi-Ethnic Study of Atherosclerosis. Am J Clin Nutr. Sep. 2008;88(3):645-50.
Dogan et al., Microstructural Control of Complex-Shaped Ceramics Processed by Freeze Casting. CFI Ceramic Forum International. May 2002;79(5);E35(1-4).
Dua et al., Liposome: Methods of Preparation and Applications. Int J. Pharm Stud Res. Apr. 2012; 3(2): 14-20.
Fox et al., Abdominal visceral and subcutaneous adipose tissue compartments: association with metabolic risk factors in the Framingham Heart Study. Circulation. Jul. 3, 2007; 116(1):39-48. Epub Jun. 18, 2007.
Gage et al., Experimental cryosurgery investigations in vivo. Cryobiology. Dec. 2009;59(3):229-43. doi: 10.1016/j.cryobiol.2009.10.001. Epub Oct. 13, 2009.
Garaulet et al., Relationship between fat cell size and number and fatty acid composition in adipose tissue from different fat depots in overweight/obese humans. Int J Obes (Lond). Jun. 2006;30(6):899-905.
Garibyan et al., Neural Selective Cryoneurolysis with Ice Slurry Injection in a Rat Model. Anesthesiology. Jul. 2020;133(1):185-194. doi: 10.1097/ALN.0000000000003124.
Garibyan et al., Subcutaneous Fat Reduction with Injected Ice Slurry. Plast Reconstr Surg. Apr. 2020; 145(4):725e-733e. doi: 10.1097/PRS.0000000000006658.
Gradinger et al., Abdominoplasty. The Art of Aesthetic Surgery: Principles and Techniques. Foad Nahai ed., 1st Ed. 2005. 74 pages.
Hackel et al., Transient opening of the perineurial barrier for analgesic drug delivery. Proc Natl Acad Sci U S A. Jul. 17, 2012;109(29):E2018-27. doi: 10.1073/pnas.1120800109. Epub Jun. 25, 2012.
Hirakawa et al., Loss and recovery of the blood-nerve barrier in the rat sciatic nerve after crush injury are associated with expression of intercellular junctional proteins. Exp Cell Res. Apr. 1, 2003;284(2):196-210. doi: 10.1016/s0014-4827(02)00035-6.
Kasza et al., Medical Ice Slurry Coolants for Inducing Targeted-Organ/Tissue Protective Cooling. Argonne National Laboratory. Jun. 2008. 9 pages.
Langert et al., Strategies for Targeted Delivery to the Peripheral Nerve. Front Neurosci. Nov. 27, 2018;12:887. doi: 10.3389/fnins.2018.00887. eCollection 2018.
Laverson, Improving abdominoplasty results: reconstruction of the linea alba sulcus by direct fat excision. Aesthet Surg J. Nov.-Dec. 2006;26(6):682-6. doi: 10.1016/j.asj.2006.10.016.
Levin et al., A pilot study of ice-slurry application for inducing laparoscopic renal hypothermia. BJU Int. Jan. 2007;99(1):166-70. Epub Nov. 10, 2006.

(56) References Cited

OTHER PUBLICATIONS

Li et al., Changes in the blood-nerve barrier after sciatic nerve cold injury: indications supporting early treatment. Neural Regen Res. Mar. 2015; 10(3): 419-424. doi: 10.4103/1673-5374.153690: 10.4103/1673-5374.153690.

Oku et al., A simple procedure for the determination of the trapped volume of liposomes. Biochim Biophys Acta. Oct. 7, 1982; 691(2): 332-340.

Peltonen et al., Barriers of the peripheral nerve. Tissue Barriers. Jul. 1, 2013;1(3):e24956. doi: 10.4161/tisb.24956. Epub May 30, 2013.

Rathmell et al., Chapter 14—Intercostal Nerve Block and Neurolysis. Atlas of Image-Guided Intervention in Regional Anesthesia and Pain Medicine. 2012. p. 201-3.

Rengachary et al., Effect of glycerol on peripheral nerve: an experimental study. Neurosurgery. Dec. 1983;13(6):681-8. doi: 10.1227/00006123-198312000-00012.

Richner et al., Functional and Structural Changes of the Blood-Nerve-Barrier in Diabetic Neuropathy. Front Neurosci. Jan. 14, 2019;12:1038. doi: 10.3389/fnins.2018.01038. eCollection 2018.

Santamaria et al., Tetrodotoxin, epinephrine, and chemical permeation enhancer combinations in peripheral nerve blockade. Anesth Analg. Jun. 2017; 124(6): 1804-1812. doi: 10.1213/ANE.0000000000002072.

Sugiritama, Histology of Nervous System. Educational Staff at Medical Faculty of Udayana University. Published Jun. 23, 2009 (available at https://www.slideshare.net/sugiritama/histologic-structure-of-nervous-system).

Van Eps et al., Distal limb cryotherapy for the prevention of acute laminitis. Clin Tech Equine Pract. Mar. 1, 2004;3(1):64-70.

Yamamoto et al., Adipose depots possess unique developmental gene signatures. Obesity (Silver Spring). May 2010;18(5):872-878. doi: 10.1038/oby.2009.512. Epub Jan. 28, 2010. Erratum in:Obesity (Silver Spring). May 2010;18(5):1064.

Yang et al., Getting Drugs across Biological Barriers. Adv Mater. Oct. 2017;29(37):10.1002/adma.201606596. doi: 10.1002/adma.201606596. Epub Jul. 28, 2017.

Yao et al., Medical Polymer Materials. Chemical Industry Press. Apr. 30, 2008;908-10.

International Search Report and Written Opinion for International Application No. PCT/US2021/014789 dated May 18, 2021.

Amasheh et al., Claudin-2 expression induces cation-selective channels in tight junctions of epithelial cells. J Cell Sci. Dec. 15, 2002;115(Pt 24):4969-76. doi: 10.1242/jcs.00165.

Antonijevic et al., Perineurial defect and peripheral opioid analgesia in inflammation. J Neurosci. Jan. 1995;15(1 Pt 1):165-72. doi: 10.1523/JNEUROSCI.15-01-00165.1995.

Begley, Delivery of therapeutic agents to the central nervous system: the problems and the possibilities. Pharmacol Ther. Oct. 2004;104(1):29-45. doi: 10.1016/j.pharmthera.2004.08.001.

Binshtok et al., Inhibition of nociceptors by TRPV1-mediated entry of impermeant sodium channel blockers. Nature. Oct. 4, 2007;449(7162):607-10. doi: 10.1038/nature06191.

Blasig et al., Occludin protein family: oxidative stress and reducing conditions. Antioxid Redox Signal. Sep. 1, 2011;15(5):1195-219. doi: 10.1089/ars.2010.3542. Epub May 5, 2011.

Blasig et al., On the self-association potential of transmembrane tight junction proteins. Cell Mol Life Sci. Feb. 2006;63(4):505-14. doi: 10.1007/s00018-005-5472-x.

Colegio et al., Claudin extracellular domains determine paracellular charge selectivity and resistance but not tight junction fibril architecture. Am J Physiol Cell Physiol. Jun. 2003;284(6):C1346-54. doi: 10.1152/ajpcell.00547.2002. Epub Apr. 16, 2003.

Coyne et al., Role of claudin interactions in airway tight junctional permeability. Am J Physiol Lung Cell Mol Physiol. Nov. 2003;285(5):L1166-78. doi: 10.1152/ajplung.00182.2003. Epub Aug. 8, 2003.

Cukierman et al., Residues in a highly conserved claudin-1 motif are required for hepatitis C virus entry and mediate the formation of cell-cell contacts. J Virol. Jun. 2009;83(11):5477-84. doi: 10.1128/JVI.02262-08. Epub Mar. 18, 2009.

Cuschieri et al., Hypertonic preconditioning inhibits macrophage responsiveness to endotoxin. J Immunol. Feb. 1, 2002; 168(3): 1389-96. doi: 10.4049/jimmunol.168.3.1389.

Fried et al., Peginterferon alfa-2a plus ribavirin for chronic hepatitis C virus infection. N Engl J Med. Sep. 26, 2002;347(13):975-82. doi: 10.1056/NEJMoa020047.

Fujita et al., Clostridium perfringens enterotoxin binds to the second extracellular loop of claudin-3, a tight junction integral membrane protein. FEBS Lett. Jul. 7, 2000;476(3):258-61. doi: 10.1016/s0014-5793(00)01744-0.

Fujita et al., Permeability characteristics of tetragastrins across intestinal membranes using the Caco-2 monolayer system: comparison between acylation and application of protease inhibitors. Pharm Res. Sep. 1998; 15(9): 1387-92. doi: 10.1023/a:1011997404306.

Furuse et al., A single gene product, claudin-1 or -2, reconstitutes tight junction strands and recruits occludin in fibroblasts. J Cell Biol. Oct. 19, 1998;143(2):391-401. doi: 10.1083/jcb.143.2.391.

Furuse et al., Claudin-based tight junctions are crucial for the mammalian epidermal barrier: a lesson from claudin-1-deficient mice. J Cell Biol. Mar. 18, 2002;156(6): 1099-111. doi: 10.1083/jcb.200110122. Epub Mar. 11, 2002.

Furuse et al., Occludin: a novel integral membrane protein localizing at tight junctions. J Cell Biol. Dec. 1993; 123(6 Pt 2): 1777-88. doi: 10.1083/jcb.123.6.1777.

Graham et al., Characteristics of a human cell line transformed by DNA from human adenovirus type 5. J Gen Virol. Jul. 1977;36(1):59-74. doi: 10.1099/0022-1317-36-1-59.

Grant et al., Perineural antinociceptive effect of opioids in a rat model. Acta Anaesthesiol Scand. Aug. 2001;45(7):906-10. doi: 10.1034/j.1399-6576.2001.045007906.x.

Hamamoto et al., Antimicrobial activity and stability to proteolysis of small linear cationic peptides with D-amino acid substitutions. Microbiol Immunol. 2002;46(11):741-9. doi: 10.1111/j.1348-0421.2002.tb02759.x.

Ikenouchi et al., Tricellulin constitutes a novel barrier at tricellular contacts of epithelial cells. J Cell Biol. Dec. 19, 2005; 171(6):939-45. doi: 10.1083/jcb.200510043.

Junger et al., Hypertonicity regulates the function of human neutrophils by modulating chemoattractant receptor signaling and activating mitogen-activated protein kinase p38. J Clin Invest. Jun. 15, 1998;101(12):2768-79. doi: 10.1172/JCI1354.

Kanda et al., Chronic inflammatory demyelinating polyneuropathy: decreased claudin-5 and relocated ZO-1. J Neurol Neurosurg Psychiatry. May 2004;75(5):765-9. doi: 10.1136/jnnp.2003.025692.

Kondoh et al., A novel strategy for the enhancement of drug absorption using a claudin modulator. Mol Pharmacol. Mar. 2005;67(3):749-56. doi: 10.1124/mol.104.008375. Epub Dec. 15, 2004.

Krause et al., Structure and function of claudins. Biochim Biophys Acta. Mar. 2008;1778(3):631-45. doi: 10.1016/j.bbamem.2007.10.018. Epub Oct. 25, 2007.

Kucenas et al., CNS-derived glia ensheath peripheral nerves and mediate motor root development. Nat Neurosci. Feb. 2008;11(2):143-51. doi: 10.1038/nn2025. Epub Jan. 6, 2008.

Labuz et al., Immune cell-derived opioids protect against neuropathic pain in mice. J Clin Invest. Feb. 2009;119(2):278-86. doi: 10.1172/JCI36246. Epub Jan. 12, 2009.

Manns et al., Peginterferon alfa-2b plus ribavirin compared with interferon alfa-2b plus ribavirin for initial treatment of chronic hepatitis C: a randomised trial. Lancet. Sep. 22, 2001;358(9286):958-65. doi: 10.1016/s0140-6736(01)06102-5.

Marsland et al., Cryogenic damage to peripheral nerves and blood vessels in the rat. Br J Anaesth. Jun. 1983;55(6):555-8. doi: 10.1093/bja/55.6.555.

Morita et al., Claudin multigene family encoding four-transmembrane domain protein components of tight junction strands. Proc Natl Acad Sci USA. Jan. 19, 1999;96(2):511-6. doi: 10.1073/pnas.96.2.511.

Mrsny et al., A key claudin extracellular loop domain is critical for epithelial barrier integrity. Am J Pathol. Apr. 2008;172(4):905-15. doi: 10.2353/ajpath.2008.070698. Epub Mar. 18, 2008.

(56) References Cited

OTHER PUBLICATIONS

Ohki et al., Interaction of melittin with lipid membranes. Biochim Biophys Acta. Sep. 14, 1994;1194(2):223-32. doi: 10.1016/0005-2736(94)90303-4.

Piña-Oviedo et al., The normal and neoplastic perineurium: a review. Adv Anat Pathol. May 2008; 15(3): 147-64. doi: 10.1097/PAP.0b013e31816f8519.

Pummi et al., Tight junction proteins ZO-1, occludin, and claudins in developing and adult human perineurium. J Histochem Cytochem. Aug. 2004;52(8): 1037-46. doi: 10.1369/jhc.3A6217.2004.

Rousset et al., Presence and cell growth-related variations of glycogen in human colorectal adenocarcinoma cell lines in culture. Cancer Res. Feb. 1979;39(2 Pt 1):531-4.

Sagie et al., Prolonged sensory-selective nerve blockade. Proc Natl Acad Sci U S A. Feb. 23, 2010;107(8):3740-5. doi: 10.1073/pnas.0911542107. Epub Feb. 4, 2010.

Simons et al., Effect of chemical permeation enhancers on nerve blockade. Mol Pharm. Jan.-Feb. 2009;6(1):265-73. doi: 10.1021/mp800167a.

Sonoda et al., Clostridium perfringens enterotoxin fragment removes specific claudins from tight junction strands: Evidence for direct involvement of claudins in tight junction barrier. J Cell Biol. Oct. 4, 1999;147(1): 195-204. doi: 10.1083/jcb.147.1.195.

Stein et al., Intrinsic mechanisms of antinociception in inflammation: local opioid receptors and beta-endorphin. J Neurosci. Apr. 1990; 10(4): 1292-8. doi: 10.1523/JNEUROSCI.10-04-01292.1990.

Takahashi et al., Role of C-terminal regions of the C-terminal fragment of Clostridium perfringens enterotoxin in its interaction with claudin-4. ontrol Release. Nov. 2, 2005;108(1):56-62. doi: 10.1016/j.jconrel.2005.07.008. Epub Aug. 8, 2005.

Todd et al., Ionic permeability of the frog sciatic nerve perineurium: parallel studies of potassium and lanthanum penetration using electrophysiological and electron microscopic techniques. J Neurocytol. Aug. 2000;29(8):551-67. doi: 10.1023/a:1011015916768.

Vietor et al., Perturbation of the tight junction permeability barrier by occludin loop peptides activates beta-catenin/TCF/LEF-mediated transcription. EMBO Rep. Apr. 2001;2(4):306-12. doi: 10.1093/embo-reports/kve066.

Weerasuriya et al., Modification of permeability of frog perineurium to [14C]-sucrose by stretch and hypertonicity. Brain Res. Sep. 21, 1979;173(3):503-12. doi: 10.1016/0006-8993(79)90244-0.

Wen et al., Selective decrease in paracellular conductance of tight junctions: role of the first extracellular domain of claudin-5. Mol Cell Biol. Oct. 2004;24(19):8408-17. doi: 10.1128/MCB.24.19.8408-8417.2004.

Winkler et al., Molecular determinants of the interaction between Clostridium perfringens enterotoxin fragments and claudin-3. J Biol Chem. Jul. 10, 2009;284(28):18863-72. doi: 10.1074/jbc.M109.008623. Epub May 8, 2009.

Wong et al., A synthetic peptide corresponding to the extracellular domain of occludin perturbs the tight junction permeability barrier. J Cell Biol. Jan. 27, 1997;136(2):399-409. doi: 10.1083/jcb.136.2.399.

Wong et al., Targeted and reversible disruption of the blood-testis barrier by an FSH mutant-occludin peptide conjugate. FASEB J. Feb. 2007;21(2):438-48. doi: 10.1096/fj.05-4144com. Epub Dec. 13, 2006.

Wu et al., Identification of new claudin family members by a novel PSI-BLAST based approach with enhanced specificity. Proteins. Dec. 1, 2006;65(4):808-15. doi: 10.1002/prot.21218.

Zimmermann, Ethical guidelines for investigations of experimental pain in conscious animals. Pain. Jun. 1983; 16(2): 109-110. doi: 10.1016/0304-3959(83)90201-4.

Zollner et al., Painful inflammation-induced increase in mu-opioid receptor binding and G-protein coupling in primary afferent neurons. Mol Pharmacol. Aug. 2003;64(2):202-10. doi: 10.1124/mol.64.2.202.

Zwanziger et al., A peptidomimetic tight junction modulator to improve regional analgesia. Mol Pharm. Jun. 4, 2012;9(6): 1785-94. doi: 10.1021/mp3000937. Epub May 10, 2012.

Carruthers et al., Cryolipolysis and skin tightening. Dermatol Surg. Dec. 2014;40 Suppl 12:S184-9. doi: 10.1097/DSS.0000000000000229.

Foster et al., Sympathetic but not sensory denervation stimulates white adipocyte proliferation. Am J Physiol Regul Integr Comp Physiol. Dec. 2006;291(6):R1630-7. doi: 10.1152/ajpregu.00197.2006. Epub Aug. 3, 2006.

Hauser, International Medical Editorial Board Consensus Statement on the Use of Prolotherapy for Musculoskeletal Pain. Journal of Prolotherapy. Dec. 2011; 3(4): 741-848.

Lapid, Syringe-Delivered Tumescent Anesthesia Made Easier. Aesthetic Plast Surg. Aug. 2011;35(4):601-2. doi: 10.1007/s00266-010-9625-4. Epub Nov. 24, 2010.

Manasse et al., Myocardial acute and chronic histological modi®cations induced by cryoablation. Eur J Cardiothorac Surg. Mar. 2000;17(3):339-40. doi: 10.1016/s1010-7940(99)00361-9.

Segev et al., Endocardial cryotherapy as a novel strategy of improving myocardial perfusion in a patient with severe coronary artery disease. Catheter Cardiovasc Interv. Oct. 2003;60(2):229-32. doi: 10.1002/ccd.10621.

Sloviter et al., Effects of the intravenous administration of glycerol solutions to animals and man. J Clin Invest. May 1958;37(5):619-26. doi: 10.1172/JCI103644.

Stevens et al., Molecular and Histological Evidence Detailing Clinically Observed Skin Improvement Following Cryolipolysis. Aesthet Surg J. May 17, 2021;sjab226. doi: 10.1093/asj/sjab226. Online ahead of print.

Stevens, Does Cryolipolysis Lead to Skin Tightening? A First Report of Cryodermadstringo. Aesthet Surg J. Aug. 2014;34(6):NP32-4. doi: 10.1177/1090820X14539699. Epub Aug. 1, 2014.

Zelickson et al., Cryolipolysis for Noninvasive Fat Cell Destruction: Initial Results from a Pig Model. Dermatol Surg. Oct. 2009;35(10): 1462-70. doi: 10.1111/j.1524-4725.2009.01259.x. Epub Jul. 13, 2009.

U.S. Appl. No. 17/629,206, filed Jan. 21, 2022, Anderson et al.

PCT/US2020/043280, dated Feb. 3, 2022, International Preliminary Report on Patentability.

EP 21200731.4, dated Mar. 2, 2022, Extended European Search Report.

International Preliminary Report on Patentability for Application No. PCT/US2020/043280, dated Feb. 3, 2022.

Extended European Search Report dated Mar. 2, 2022 for Application No. EP 21200731.4.

\* cited by examiner

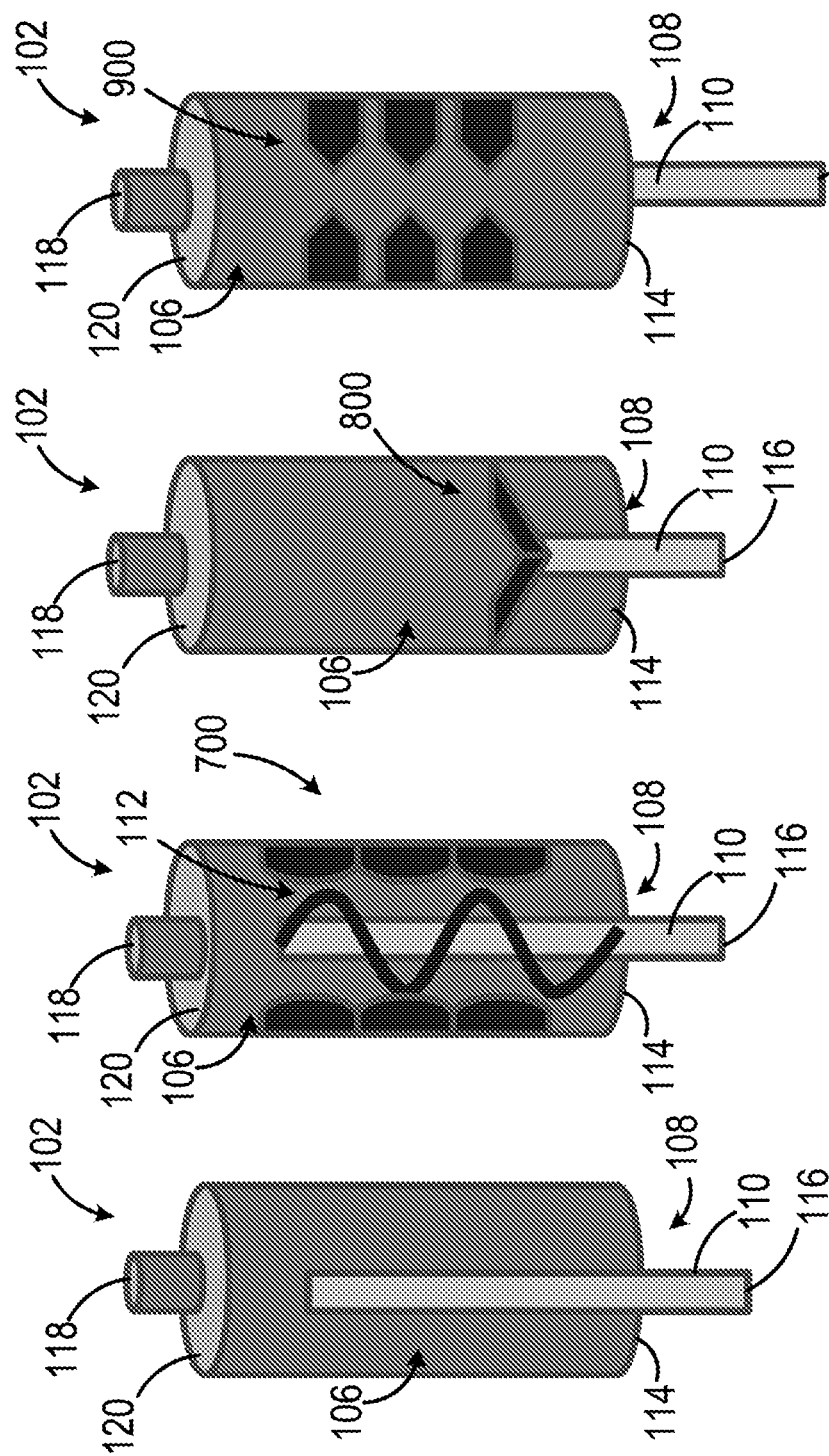

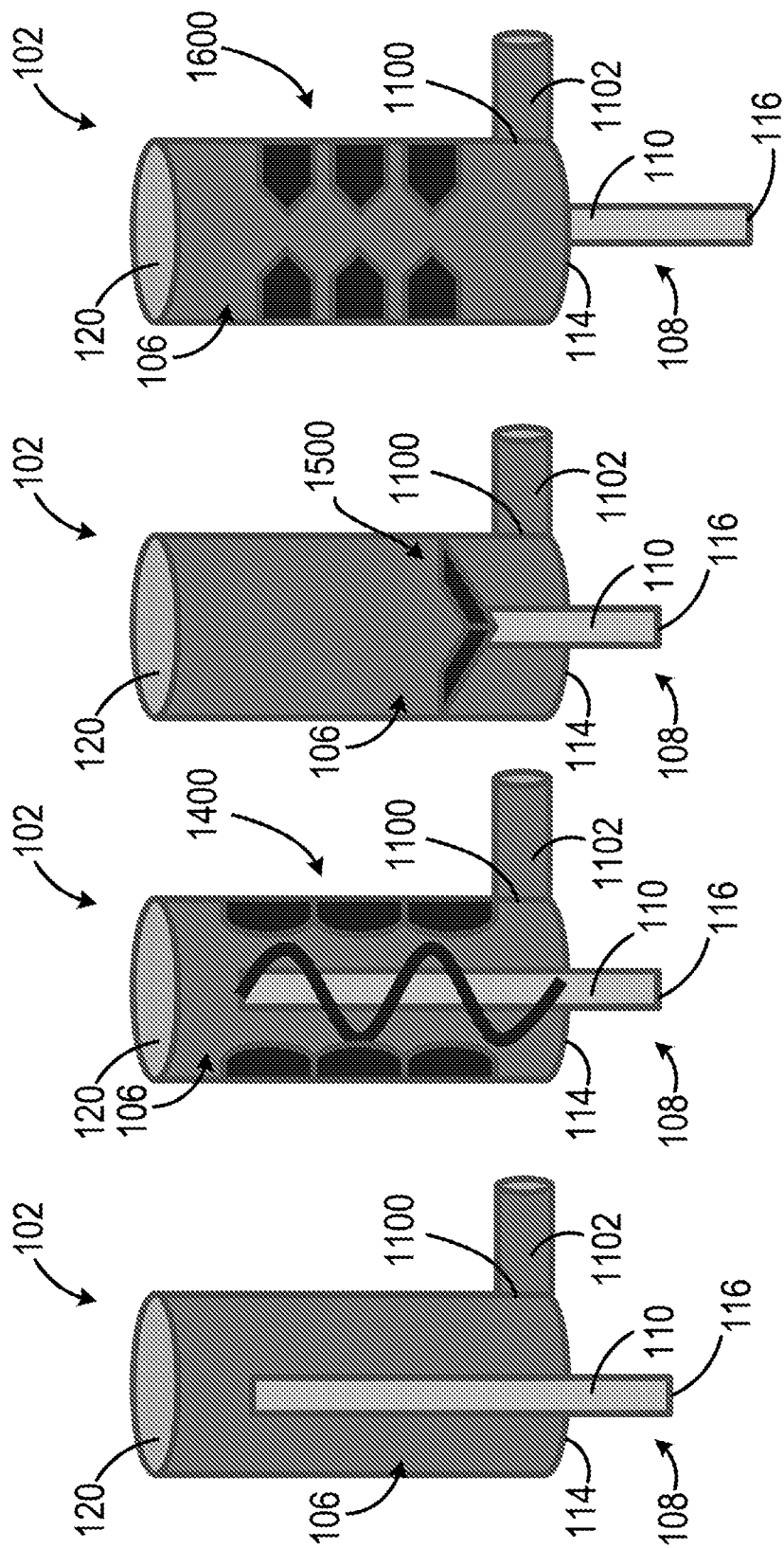

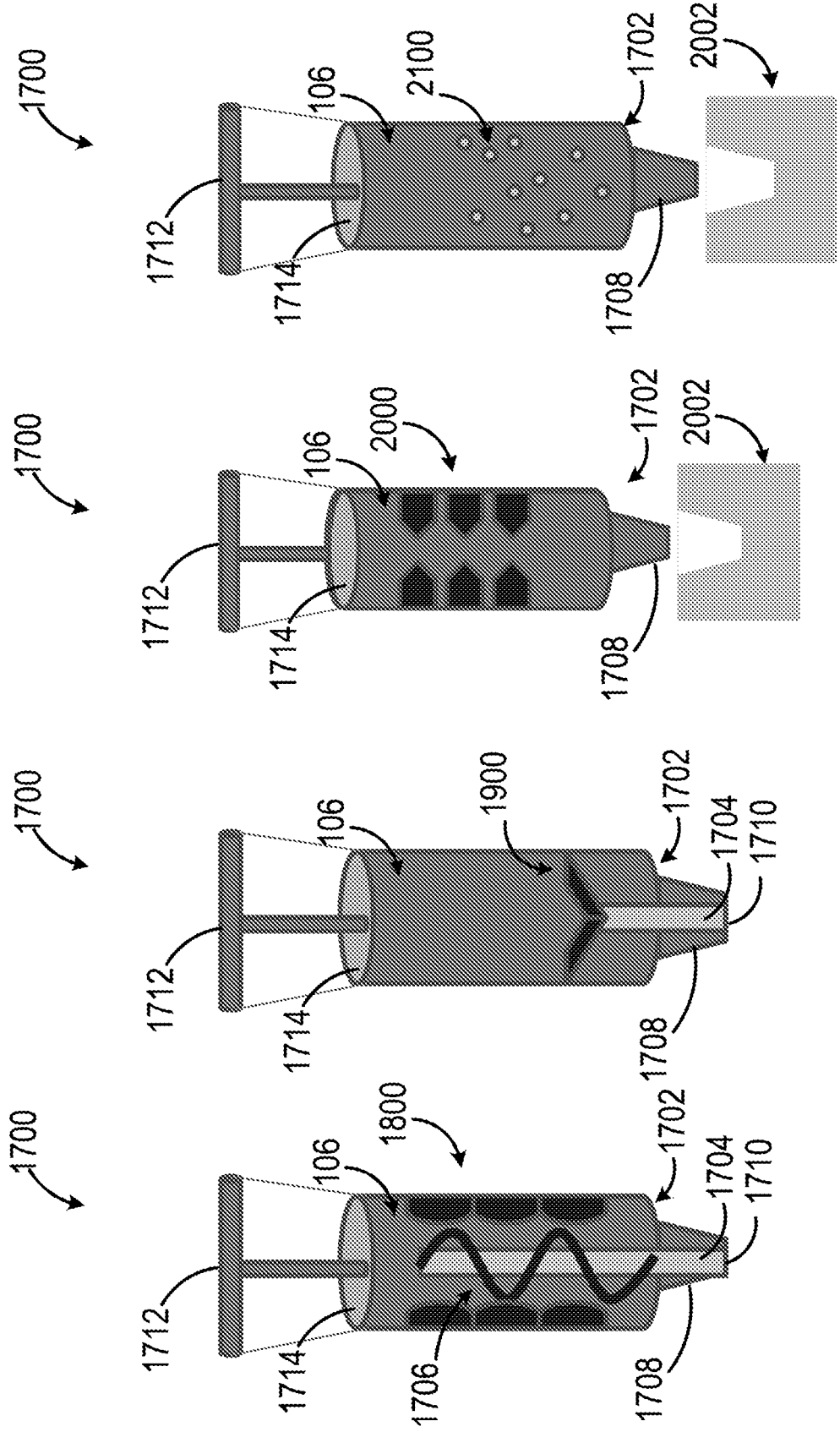

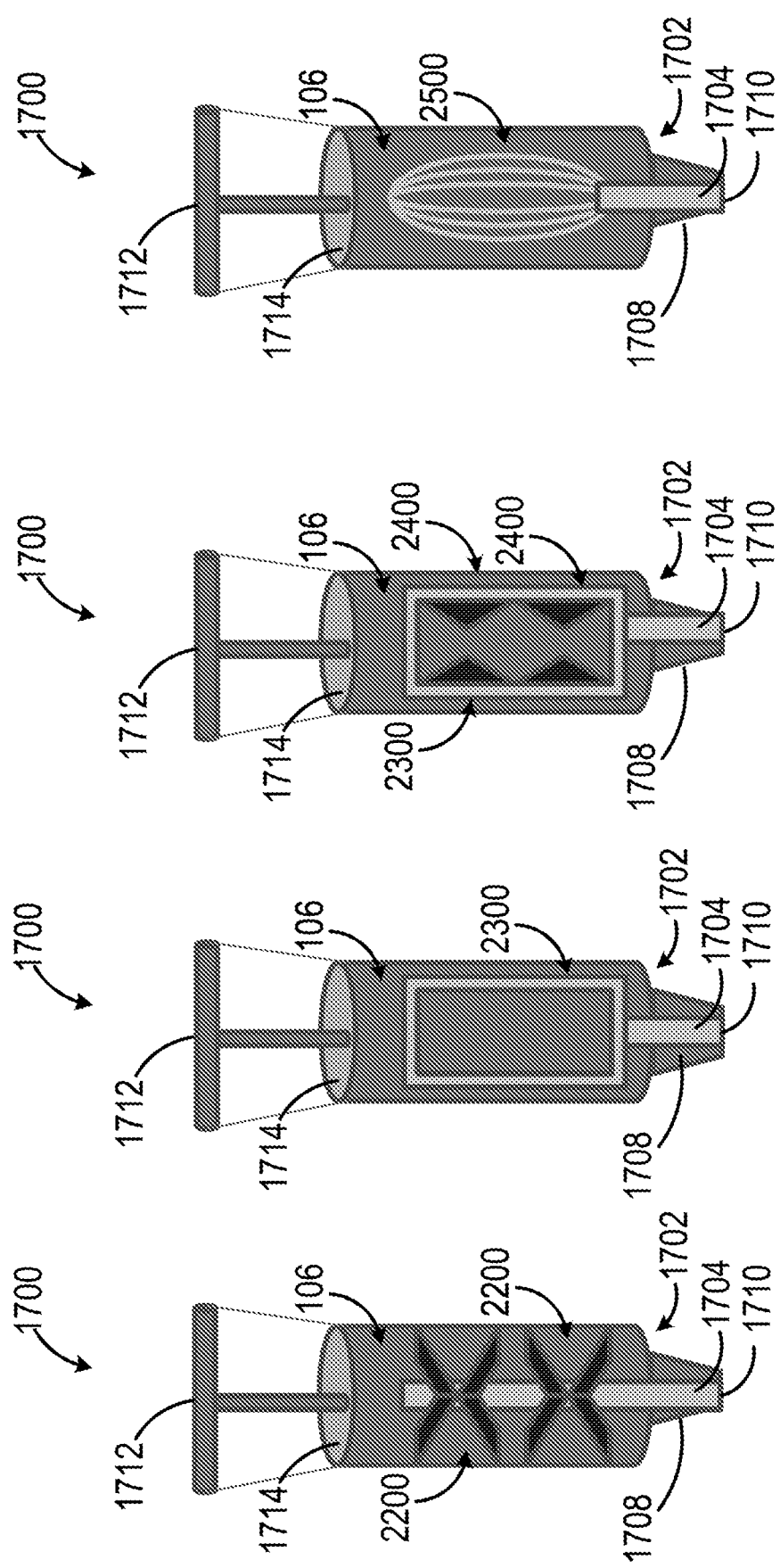

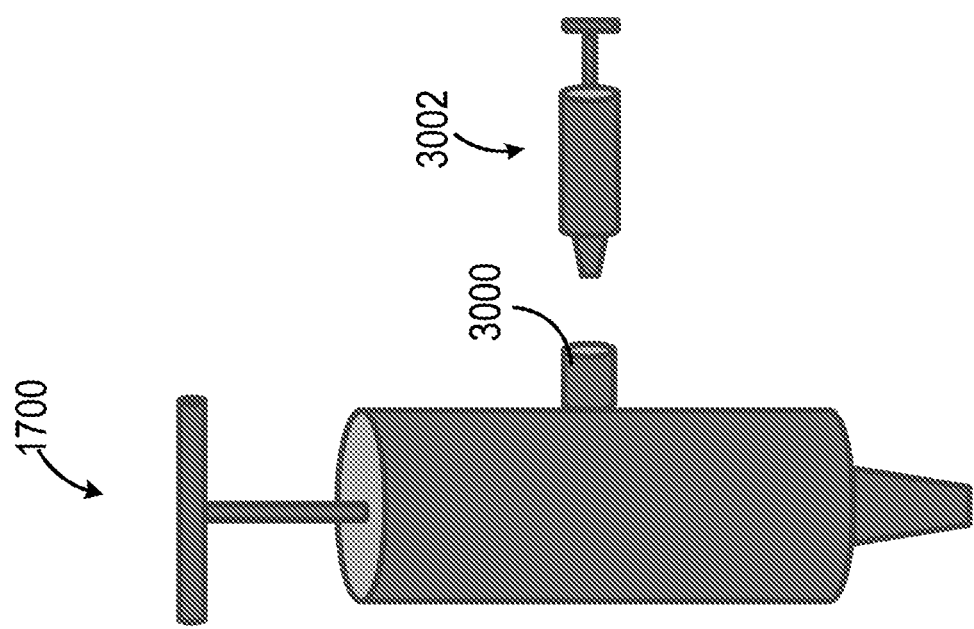
FIG. 33
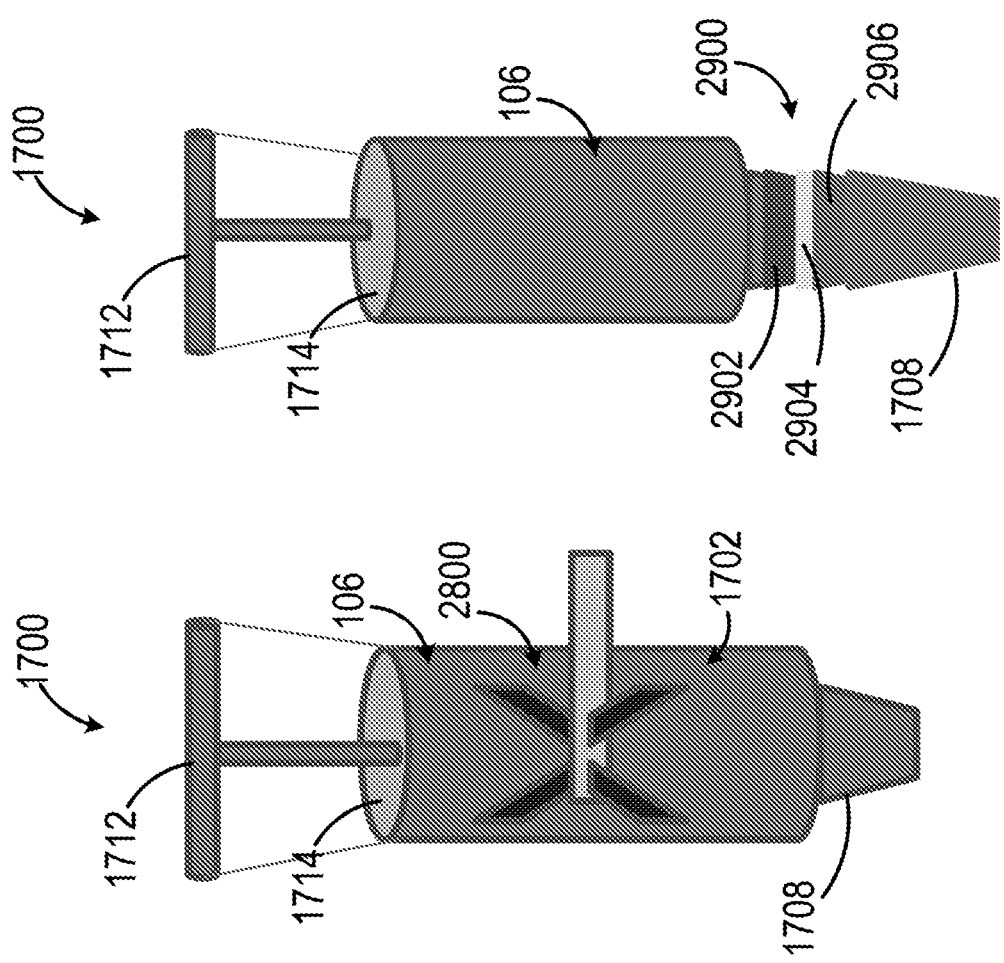
FIG. 32
FIG. 31

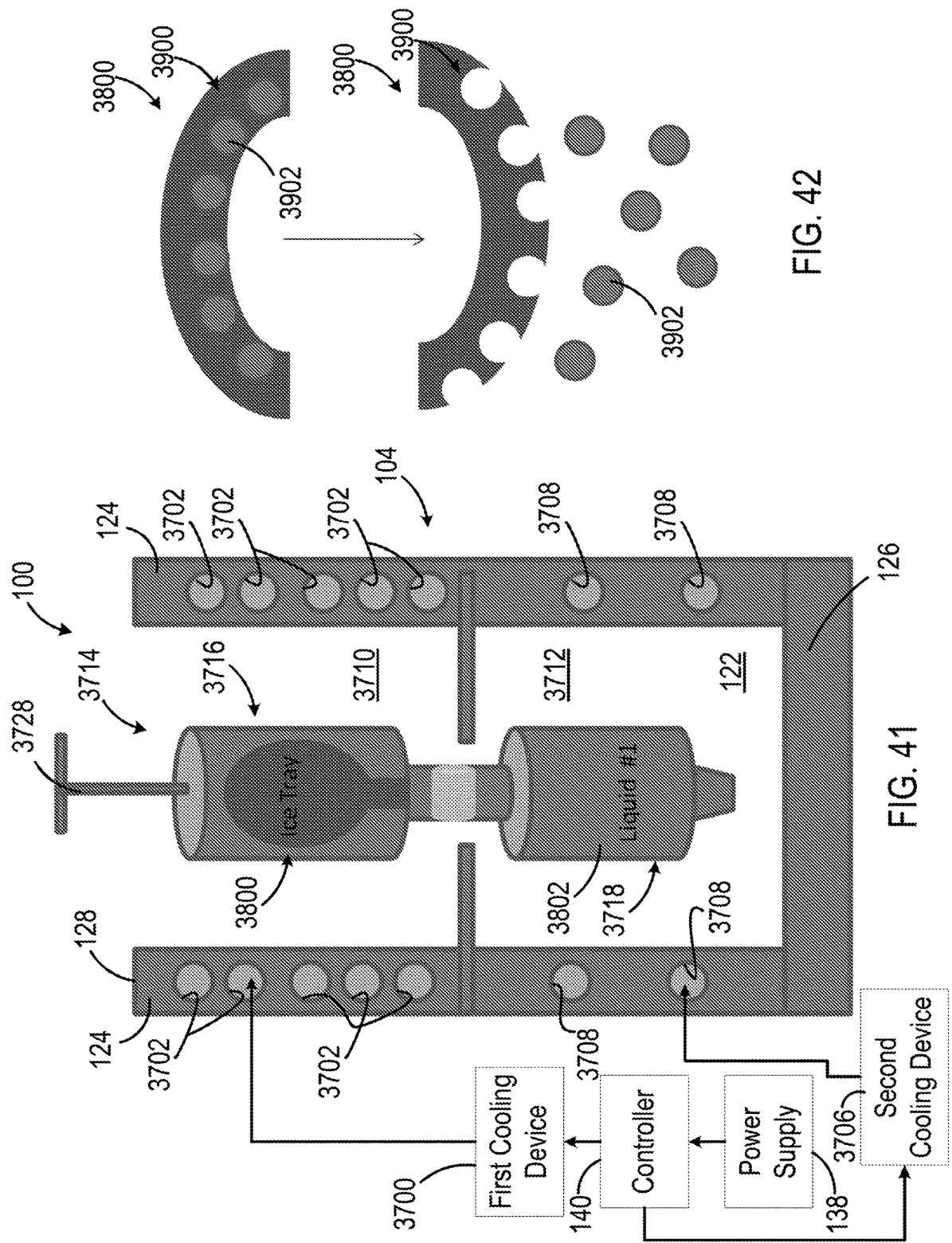

MEDICAL ICE SLURRY PRODUCTION AND DELIVERY SYSTEMS AND METHODS

CROSS-REFERENCES TO RELATED APPLICATIONS

The present application is a U.S. National Phase of PCT Application No. PCT/US2017/019268 filed on Feb. 24, 2017 which is based on and claims priority to U.S. Provisional Patent Application No. 62/300,679, filed Feb. 26, 2016, each of which is incorporated herein by reference in its entirety.

STATEMENT REGARDING FEDERALLY SPONSORED RESEARCH

Not Applicable.

BACKGROUND

The disclosure relates generally to ice slurries for medical use and, more specifically, to systems and methods for medical ice slurry production and withdrawal or injection.

Ice slurries used in medical applications typically comprise a partially frozen saline solution. Medical ice slurries are used in surgical applications to induce therapeutic hypothermia and slow organ and tissue metabolic rates thereby protecting a patient's organs during a surgical procedure. Medical ice slurries are also injected into a patient for selective or non-selective cryotherapy and/or cryolysis.

BRIEF SUMMARY

The present disclosure provides systems and method for medical ice slurry production. In particular, medical ice slurry production systems and methods are disclosed that enable an end user/clinician to produce and deliver a sterile medical ice slurry composition at the point of care.

In one aspect, the present disclosure provides a medical ice slurry production system including a disposable cartridge holding a non-frozen, sterile medical slurry composition. The system further includes a housing supporting the disposable cartridge. The housing includes an actuator, and a cooling device operable with the housing to cool the non-frozen slurry composition held in the disposable cartridge to a temperature sufficient to form ice crystals. The medical ice slurry production system further includes an agitator operable with the actuator of the housing to agitate the medical slurry composition such that the ice crystals are reduced to a size sufficient to allow the medical slurry composition including the reduced ice crystals to be delivered to a patient through an end of a needle, and an access port structured and arranged to allow the medical slurry composition including the reduced ice crystals to be withdrawn or injected from the disposable cartridge, while maintaining the sterility of the medical slurry composition including the reduced ice crystals.

In yet another aspect, the present disclosure provides a medical ice slurry production system including a disposable cartridge holding a non-frozen, sterile, medical slurry composition. The disposable cartridge includes an access port. The medical ice slurry production system further includes a housing supporting the disposable cartridge. The housing including an actuator. The medical ice slurry production system further includes a cooling device operable with the housing so as to cool the non-frozen slurry composition held in the disposable cartridge to a temperature sufficient to form ice crystals in the composition, an agitator operable with the actuator of the housing to agitate the medical slurry composition such that the ice crystals are reduced to a size sufficient to allow the medical slurry composition including the reduced ice crystals to be delivered to a patient through an end of a needle, and a pump operable to pump the medical slurry composition including the reduced ice crystals out of the access port of the disposable cartridge through a disposable delivery tube, while maintaining the sterility of the medical slurry composition including the reduce ice crystals.

In still another aspect, the present disclosure provides a medical ice slurry production method including placing, in a housing, a disposable cartridge holding a non-frozen, sterile medical slurry composition, and while placed in the housing, cooling the disposable cartridge to a temperature sufficient to form ice crystals inside the disposable cartridge. The medical ice slurry production method further includes agitating the medical slurry composition held in the disposable cartridge such that the ice crystals inside the disposable cartridge are reduced to a size sufficient to allow the medical slurry composition including the reduced ice crystals to be delivered to a patient through an end of a needle.

The foregoing and other aspects and advantages of the invention will appear from the following description. In the description, reference is made to the accompanying drawings which form a part hereof, and in which there is illustrated by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 8 illustrates a disposable cartridge of the medical ice slurry production system of FIG. 1 with another non-limiting example of an agitator.

FIG. 9 illustrates a disposable cartridge of the medical ice slurry production system of FIG. 1 with yet another non-limiting example of an agitator.

FIG. 10 illustrates a disposable cartridge of the medical ice slurry production system of FIG. 1 with still another non-limiting example of an agitator.

FIG. 11 illustrates a disposable cartridge of the medical ice slurry production system of FIG. 1 with another non-limiting example of an agitator.

FIG. 16 illustrates a disposable cartridge of the medical ice slurry production system of FIG. 11 with another non-limiting example of an agitator.

FIG. 17 illustrates a disposable cartridge of the medical ice slurry production system of FIG. 11 with yet another non-limiting example of an agitator.

FIG. 18 illustrates a disposable cartridge of the medical ice slurry production system of FIG. 11 with still another non-limiting example of an agitator.

FIG. 19 illustrates a disposable cartridge of the medical ice slurry production system of FIG. 11 with another non-limiting example of an agitator.

FIG. 21 illustrates a disposable cartridge of the medical ice slurry production system of FIG. 20 with another non-limiting example of an agitator.

FIG. 22 illustrates a disposable cartridge of the medical ice slurry production system of FIG. 20 with yet another non-limiting example of an agitator.

FIG. 23 illustrates a disposable cartridge of the medical ice slurry production system of FIG. 20 with still another non-limiting example of an agitator.

FIG. 24 illustrates a disposable cartridge of the medical ice slurry production system of FIG. 20 with another non-limiting example of an agitator.

FIG. 25 illustrates a disposable cartridge of the medical ice slurry production system of FIG. 20 with another non-limiting example of an agitator.

FIG. 26 illustrates a disposable cartridge of the medical ice slurry production system of FIG. 20 with yet another non-limiting example of an agitator.

FIG. 27 illustrates a disposable cartridge of the medical ice slurry production system of FIG. 20 with still another non-limiting example of an agitator.

FIG. 28 illustrates a disposable cartridge of the medical ice slurry production system of FIG. 20 with another non-limiting example of an agitator.

FIG. 31 illustrates a disposable cartridge of the medical ice slurry production system of FIG. 20 with still another non-limiting example of an agitator arranged on a side thereof.

FIG. 32 illustrates a disposable cartridge of the medical ice slurry production system of FIG. 20 with one or more filters arranged therein.

FIG. 33 illustrates a disposable cartridge of the medical ice slurry production system of FIG. 20 with an additive port.

FIG. 41 is a schematic illustration of a medical ice slurry production system according to still another non-limiting example of the present disclosure.

FIG. 42 illustrates an ice tray of the medical ice slurry production system of FIG. 41.

DETAILED DESCRIPTION

Medical ice slurries manufactured off-site (i.e., not at the point of care) require cold chain shipping to deliver the ice slurries to a point of care. Off-site production places substantial burdens on end users/clinicians administering an ice slurry to a patient. For example, the ice slurry must be kept sterile to ensure patient safety. The ice slurry must also be maintained at an appropriate temperature to preserve the slurry's ice crystal size, crystal shape and ice content and to ensure that the slurry maintains its cooling capabilities and ability to be injected through needles (i.e., stability). Off-site ice slurry manufacturing can therefore require end clinician's manipulation of the ice slurry, which can potentially jeopardize patient safety and/or effectiveness of the ice slurry.

It would therefore be desirable to have a medical ice slurry production system that enables an end user to produce and deliver a sterile medical ice slurry at the point of care. A system that produces the medical ice slurry at the point of care while maintaining the sterility and stability (e.g., ice crystal size and shape, and ice content) of the slurry can reduce the burdens imposed on end users and simplify the overall process of producing and delivering medical ice slurries to a patient.

Figure 1:
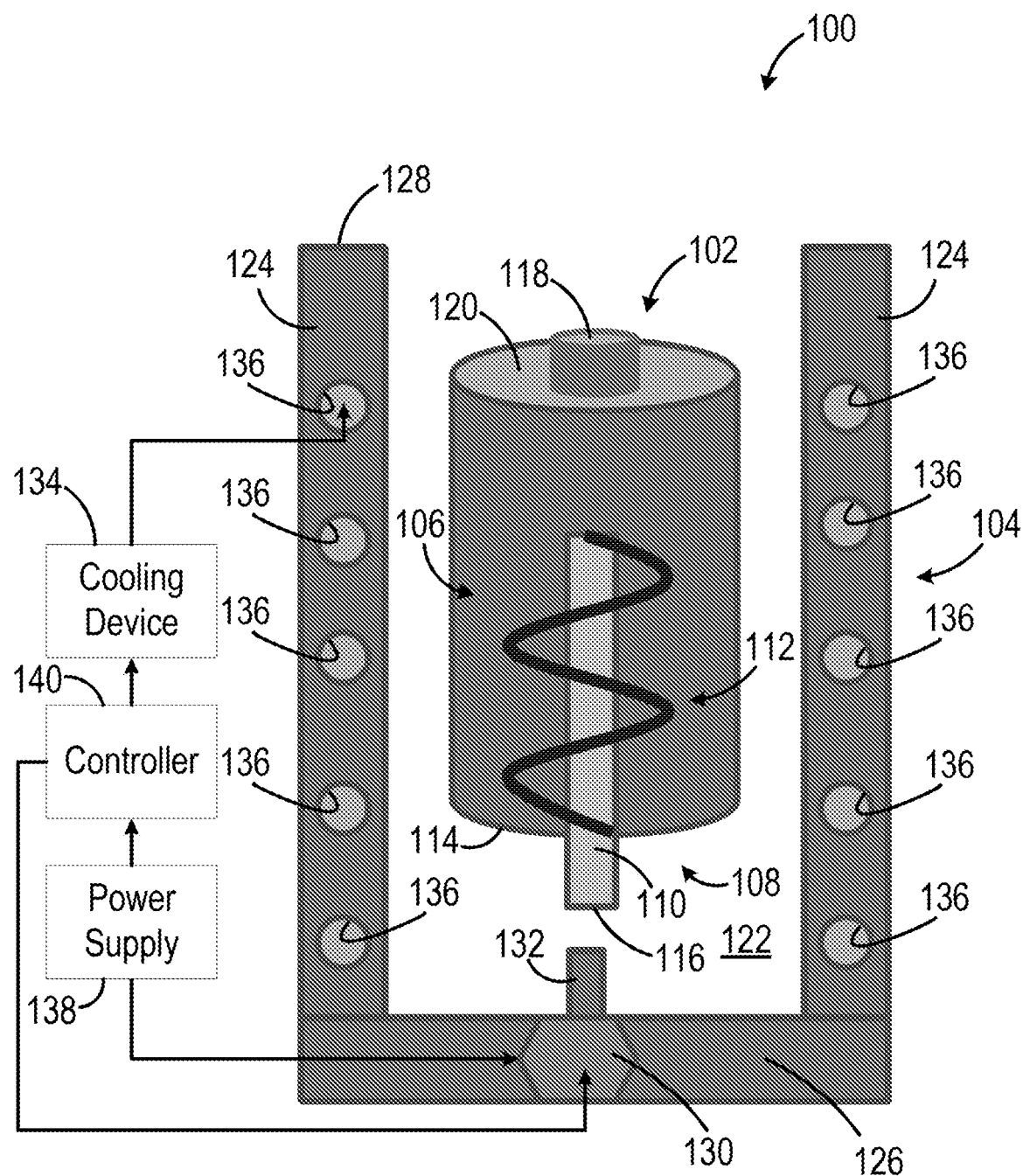
FIG. 1 is a schematic illustration of a medical ice slurry production system according to one non-limiting example of the present disclosure.

FIG. 1 illustrates one non-limiting example of a medical ice slurry production system 100. The medical ice slurry production system 100 includes a disposable cartridge 102 configured to be supported within a housing 104. The illustrated disposable cartridge 102 is in the form of a sterile pre-filled canister. The disposable cartridge 102 is pre-filled with a sterile slurry composition 106. For example, the disposable cartridge 102 may be pre-filled with one of the slurry compositions described in International Patent Application No. PCT/US2015/047301, which is incorporated herein by reference in its entirety. As described, for example, in PCT/US2015/047301, such slurry compositions can have preferred ice content ranges, temperature ranges, and include one or more added ice particle smoothing agents and/or biocompatible surfactants (e.g., glycerol), which can, for example, make the slurry more injectable. In any of the systems described herein, it can be preferable to add such agents or surfactants after the systems agitate, blend, mix or pulverize the medical ice slurry (as described below), and right before the slurry is injected. Pre-filling the disposable cartridge 102 with the sterile slurry composition 106 ensures the sterile slurry composition 106 is self-contained within a closed environment. This helps relieve an end user's burden of trying to maintain sterility of the slurry composition 106 while handling the disposable cartridge 102. In some non-limiting examples, the disposable cartridge 102 may be surrounded by insulation (not shown) to improve thermal stability.

The disposable cartridge 102 can be fabricated from a plastic, glass, or metal material. The disposable cartridge 102 can be dimensioned to hold a slurry volume between approximately one cubic centimeter (cc) and approximately one liter (L) depending on the medical application. The disposable cartridge 102 is rotationally coupled to an agitator 108. The agitator 108 includes an agitator shaft 110 and a fin 112 arranged within the disposable cartridge 102. Fin 112 is coupled to the agitator shaft 110 and spirals lengthwise along the shaft 110. Agitator shaft 110 is partially received within the disposable cartridge 102. That is, agitator shaft 110 is received in a first side 114 of the disposable cartridge 102 such that a distal end 116 of the agitator shaft 110 protrudes from the first end 114 of the disposable cartridge 102. The agitator shaft 110 is rotationally sealed to the first end 114 of the disposable cartridge 102 to allow rotation of the agitator shaft 110 with respect to the disposable cartridge 102 while maintaining a seal between the sterile slurry composition 106 and the surrounding environment. The seal between the agitator shaft 110 and the first end 114 of the disposable cartridge 102 can be obtained by utilizing, for example, at least one of a sealed hydrostatic, a sealed hydrodynamic, a fluid bearing, or an o-ring.

The disposable cartridge 102 includes an access port 118 arranged in a second side 120 of the disposable cartridge 102. Access port 118 is structured and arranged to allow the medical ice slurry composition 106 to be withdrawn from the disposable cartridge 102 while maintaining the sterility of the slurry composition 106. For example, access port 118 can be configured to allow the medical ice slurry composition to be withdrawn from the access port using a syringe. Alternatively or additionally, a user could pump the medical ice slurry composition fluid from the access port using a pump and a disposable delivery tube, as discussed in more detail below. In certain implementations, the pumps or the controllers configured to operate the pumps can be configured to have a maximum allowable pressure tolerance at the end of the delivery tube, delivery needle or cannula. The pumps can include adjustable constant-volume pumps, and the pumps or the controllers configured to operate the pumps can be configured with user-specified stops that occur when a predefined volume of slurry has been delivered. A user could also allow the medical ice slurry composition to be withdrawn from the access port via gravity flow. It should be appreciated that the location of the access port 18 on the disposable cartridge 102 is not meant to be limiting in any way and that access port 118 can be arranged in other locations on disposable cartridge 102.

Figure 2:
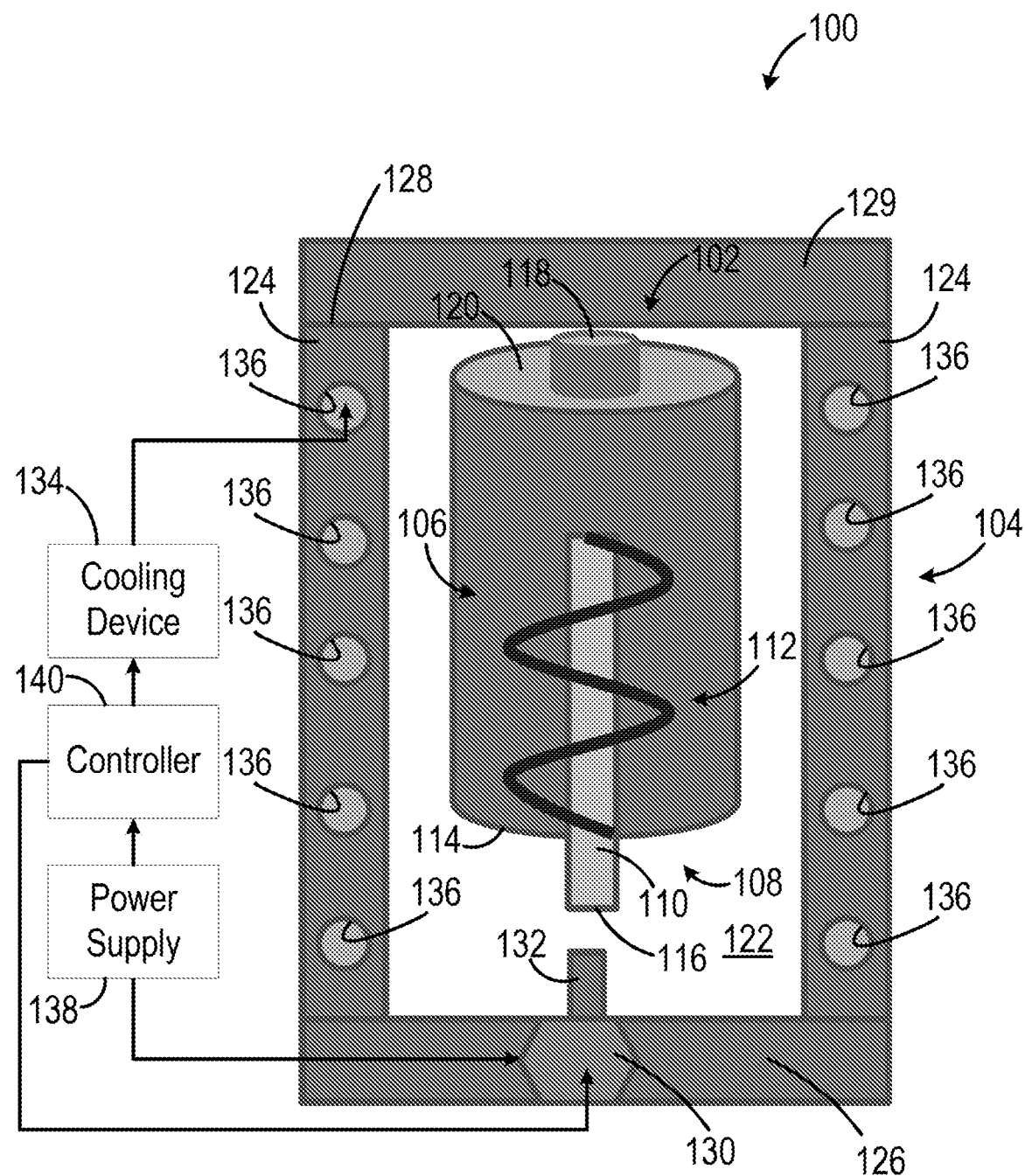
FIG. 2 illustrates the medical ice slurry production system of FIG. 1 with a cover.

The housing 104 defines an internal cavity 122 dimensioned to receive the disposable cartridge 102 and includes a pair of opposing side walls 124 extending from a base 126. Side walls 124 extend from the base 126 to a substantially open top side 128. In other non-limiting examples, housing 104 may include a removable cover 129 attached to the substantially open top side 128 to further insulate the internal cavity 122 from the surrounding environment, as shown in FIG. 2.

With continued reference to FIG. 1, the base 126 of the housing 104 includes an actuator 130 that is coupled to an actuator shaft 132. The actuator shaft 132 extends into the internal cavity 122 of the housing 104 and is configured to operably couple to the agitator shaft 110. The illustrated actuator 130 can be in the form of a motor. Alternatively or additionally, actuator can be configured to vibrate or agitate the actuator shaft 132 and thereby the disposable cartridge 102 at a given frequency (e.g., an ultrasonic frequency). In other non-limiting examples, the actuator 130 may be in the form of another rotational or vibrational mechanism known in the art. Actuator 130 is configured to selectively rotate the actuator shaft 132 and, when coupled to the agitator shaft 110, induce a turbulent agitation or mixing of the sterile slurry composition 106 within the disposable cartridge 102.

The medical ice slurry production system 100 includes a cooling device 134. In one example, the cooling device 134 is at least partially supported within the housing 104. In the illustrated non-limiting example of FIG. 1, side walls 124 of housing 104 define a passageway 136 extending between the top side 128 and the base 126. In one non-limiting example, the passageway 136 can define a substantially helical path through the side walls 124. The passageway 136 is configured to receive a cooling liquid or gas provided by the cooling device 134. Alternatively or additionally, the cooling liquid or gas provided by the cooling device 134 can be provided to a coil (e.g., a copper coil), which can be received within the passageway 136. The cooling device 134 may comprise, for example, a condenser, a compressor, and an evaporator. In other non-limiting examples, the cooling device 134 may utilize magnetic refrigeration, electrical cooling, chemical cooling, conventional refrigeration, compressed gas (Joule-Thompson) cooling, thermoelectric (Peltier) cooling, or another slurry other than the sterile slurry composition 106. The housing 104 can be fabricated from a material with a high thermal conductivity (e.g., stainless steel, copper, aluminum) to reduce a thermal resistance between the sterile slurry composition 106 within the disposable cartridge 102 and the cooling liquid or gas within the passageway 136. It should be appreciated that, in some non-limiting examples, the housing 104 can be fabricated from one or more materials. For example, an interior portion of the housing 104 adjacent to the disposable cartridge 102 can be fabricated from a material with a high thermal conductivity, and an exterior portion of the housing 104 can be fabricated from an insulating material (e.g., plastic or foam).

A power supply 138 supplies electrical power to the cooling device 134, the actuator 130, and a controller 140. The power supply 138 may be in the form of AC wall power. Alternatively or additionally, the power supply 138 may be in the form of a portable DC power supply (e.g., a battery) to facilitate portability of the medical ice slurry production system 100. The controller 140 is in electrical communication with the actuator 130 and the cooling device 134 and configured to selectively instruct the actuator 130 to rotate the actuator shaft 132 at a desired rotational speed. The controller 140 is further configured to control the cooling device 134 and thereby control the temperature of the cooling liquid or gas within the passageway 136. One or more sensors (not shown) may be in communication with the controller 140 to sense, for example, a temperature of the cooling liquid or gas within the passageway 136, and a temperature of the sterile slurry composition 106 within the disposable cartridge 102. The temperature of the cooling liquid or gas within the passageway 136 and the temperature of the sterile slurry composition 106 may be measuring using by a thermocouple, a thermistor, or another electrical temperature sensor known in the art. Alternatively or additionally, a radiant temperature sensor can be implemented such as infrared detectors and pyroelectric sensors. The one or more sensors can provide feedback to controller 140 to enable the controller 140 to actively control the cooling device 134 to achieve and maintain a desired temperature of the sterile medical ice slurry composition 106.

Figure 3:
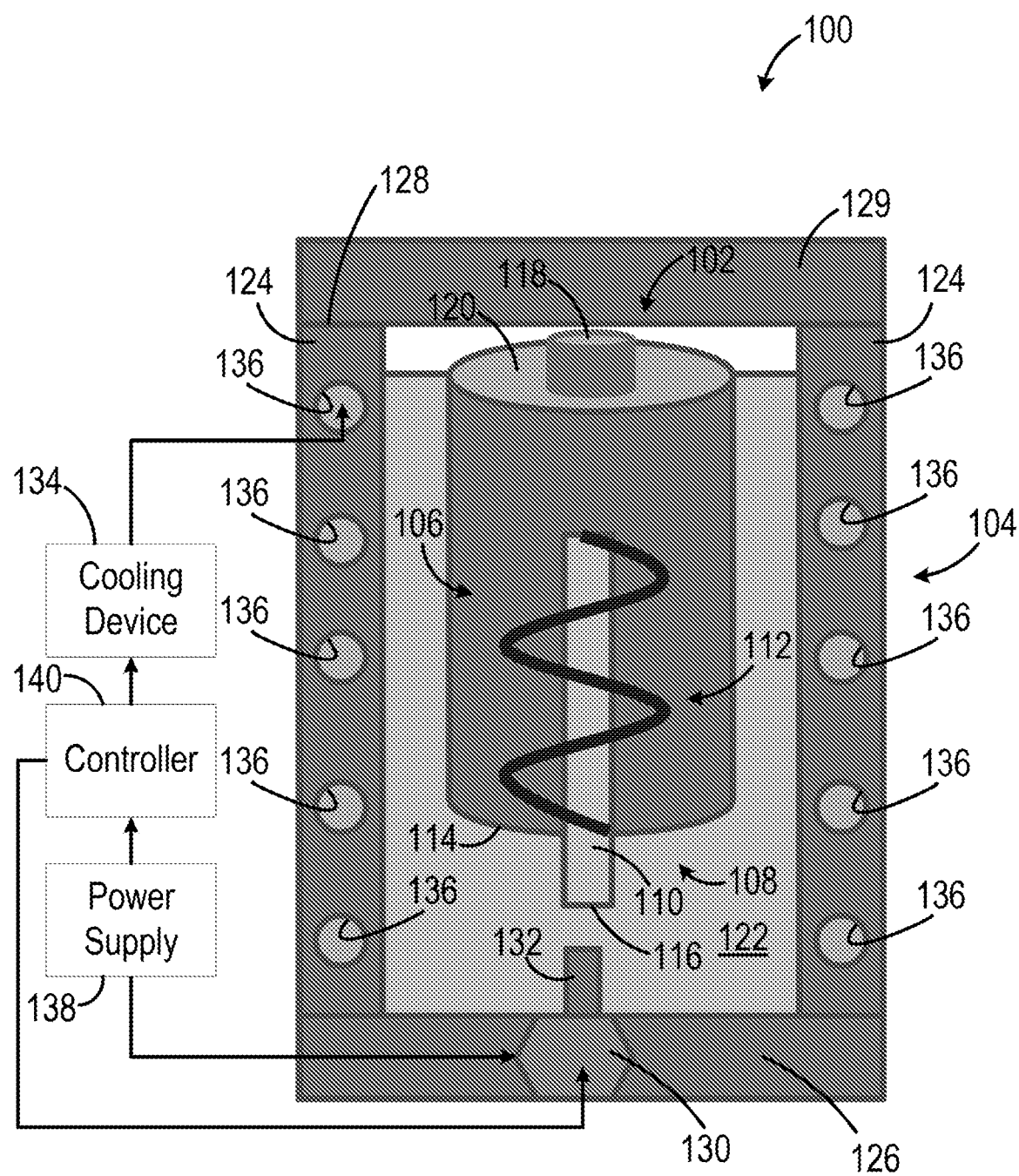
FIG. 3 illustrates the medical ice slurry production system of FIG. 1 with a liquid in an internal cavity defined by a housing.

In operation, the housing 104 of the medical ice slurry production system 100 is placed at the point of care (e.g., near a patient). The disposable cartridge 102 having a pre-filled, non-frozen sterile slurry composition 106 is then placed within the internal cavity 122 of the housing 104 and the agitator shaft 110 is coupled to the actuator shaft 132 for rotation therewith. In some non-limiting examples, the internal cavity 122 of the housing includes gas or air. In other non-limiting examples, the internal cavity 122 can be filled with a liquid, as illustrated in FIG. 3. The controller 140 is configured to instruct the cooling device 134 to cool the liquid or gas within the passageway 136 to a desired temperature (i.e. a temperature that causes ice crystals to form in the slurry composition held within the cartridge 102). In one non-limiting example, a desired temperature of the sterile slurry composition 106 may be input to the controller 140, and the controller 140 can automatically control the cooling device 134 to reach and maintain the desired slurry temperature. In some non-limiting examples, the desired temperature of the sterile slurry composition can be between approximately $-10°$ C. and approximately $4°$ C.

While the cooling device 134 is cooling the temperature of the sterile slurry composition 106 within the disposable cartridge 102, the controller 140 is configured to instruct the actuator 130 to rotate the actuator shaft 132 and thereby the agitator shaft 110. It should be appreciated that the actuator 130 can be instructed to rotate the actuator shaft 132 before, simultaneously with, or after the cooling device 134 starts cool the disposable cartridge 102. Alternatively or additionally, the disposable cartridge 102 may be precooled remotely from the housing 104 and then further cooled within the housing 104 to form the ice crystals. A desired rotation speed or amount of force provided by the actuator 130 may be input to the controller 140. In some non-limiting examples, the desired rotational speed provided by the actuator 130 may be between approximately 100 revolutions per minute (rpm) and 45,000 rpm, or between approximately 5000 rpm and 40,000 rpm, or between approximately 10,000 rpm and 30,000 rpm. Rotation of the agitator shaft 110 results in the rotation of the fin 112 within the sterile slurry composition 106. Rotating fin 112 acts to turbulently mix the sterile slurry composition 106 serving multiple purposes. First, the turbulent mixing promotes a uniform temperature distribution in the sterile slurry composition 106. Second, rotation of the fin 112 acts to break up the ice crystals that form in the sterile, slurry composition as the sterile slurry mixture 106 is cooled (i.e., the sterile slurry composition 106 transitions from a liquid composition to an ice slurry comprised of solid ice crystals and liquid). Alternatively or additionally, the controller 140 can be configured to maintain a homogeneity of the sterile slurry composition 106 once the ice crystals have formed to prevent the slurry from separating. The controller 140 may be configured to instruct the actuator 130 to provide rotation between approximately 60 rpm and 5000 rpm to preserve homogeneity of the sterile slurry composition 106, or between approximately 500 rpm and 4000 rpm, or between approximately 1500 rpm an 2500 rpm.

The agitator 108 can be structured to ensure that the ice crystals formed within the sterile slurry composition 106 are broken up to a specific ice crystal size. In one non-liming example, the ice crystals formed in the sterile slurry composition 106 can be broken up to a size of less than approximately one millimeter (mm). In another non-limiting and optimal example, the ice crystals formed in the sterile slurry composition 106 can be broken up to a size of less than approximately 0.1 mm. The size of the ice crystals in the sterile slurry composition 106 may be verified, for example, by using (i) a light/laser diffraction method, (ii) a direct measurement via microscopy, and/or (iii) an ultrasound, or acoustic, method. In some non-limiting examples, this measured size of the ice crystals in the sterile slurry composition 106 is communicated to the controller 140.

In certain embodiments, controller 140 or any of the other controllers for any of the other embodiments described herein can be configured to perform according to two different cycles of agitation. In a first cycle, the controller of any embodiment herein can be configured to instruct the actuator and hence the actuator shaft and agitator shaft (or any other agitating elements described herein) to agitate such that the ice crystals are broken down or pulverized into a size small enough to be of injectable quality (e.g., less than approximately 1 mm or preferably less than approximately 0.1 mm). In a second cycle, which can prior to or after the first cycle, the controller can be configured to instruct the actuator and hence the actuator shaft and agitator shaft (or any other agitating elements described herein) to agitate such that the slurry is adequately mixed. For example, any of the systems herein can be configures with a controller that provides rotation of the agitator or agitating element between approximately 60 rpm and 5000 rpm to ensure or preserve adequate mixing or homogeneity of the slurry, or between approximately 500 rpm and 4000 rpm, or between approximately 1500 rpm an 2500 rpm, or any other suitable speed and/or number of revolutions of the agitating element.

In some non-limiting examples, the cooling device 134 can be further configured as a cooling and heating device to provide both cooling and heating to the sterile slurry composition 106. This can enable the medical ice slurry production system 100 to first form ice crystals within the sterile slurry composition 106, and then provide heating prior to injection to ensure the formation of homogenous, globular, and non-dendritic ice crystals.

Once the sterile slurry composition 106 is cooled to the desired slurry temperature and the ice crystals within the sterile slurry composition 106 are the desired size, the sterile slurry composition 106 is withdrawn from the disposable cartridge 102 via the access port 118 for use in a desired medical application on a patient. The disposable cartridge 102 can then be disposed and the above-described process can be repeated with a new disposable cartridge 102.

As described above, an end user or clinician may only be required to place the pre-filled disposable cartridge 102 within the internal cavity 122 of the housing 104 and withdraw the sterile slurry composition 106 from the access port 118 for delivery to the patient after the slurry composition reaches a desired temperature with the desired ice crystal size. The sterile slurry composition 106 is therefore maintained within the disposable cartridge 102 throughout the ice slurry production process until the sterile ice slurry composition 106 is withdrawn for use in a patient (e.g., withdrawn for use in another sterile delivery mechanism like a syringe). It should therefore be appreciated that the sterile slurry composition 106 is self-contained throughout the medical ice slurry production process thereby reducing a clinician's burden of maintaining the sterility of the slurry composition 106. Also, the production (i.e., the cooling and forming of the properly sized ice crystals) of the sterile slurry composition 106 for the given medical application is substantially automated via controller 140, cooling device 134, and actuator 130 operating together.

Figure 4:
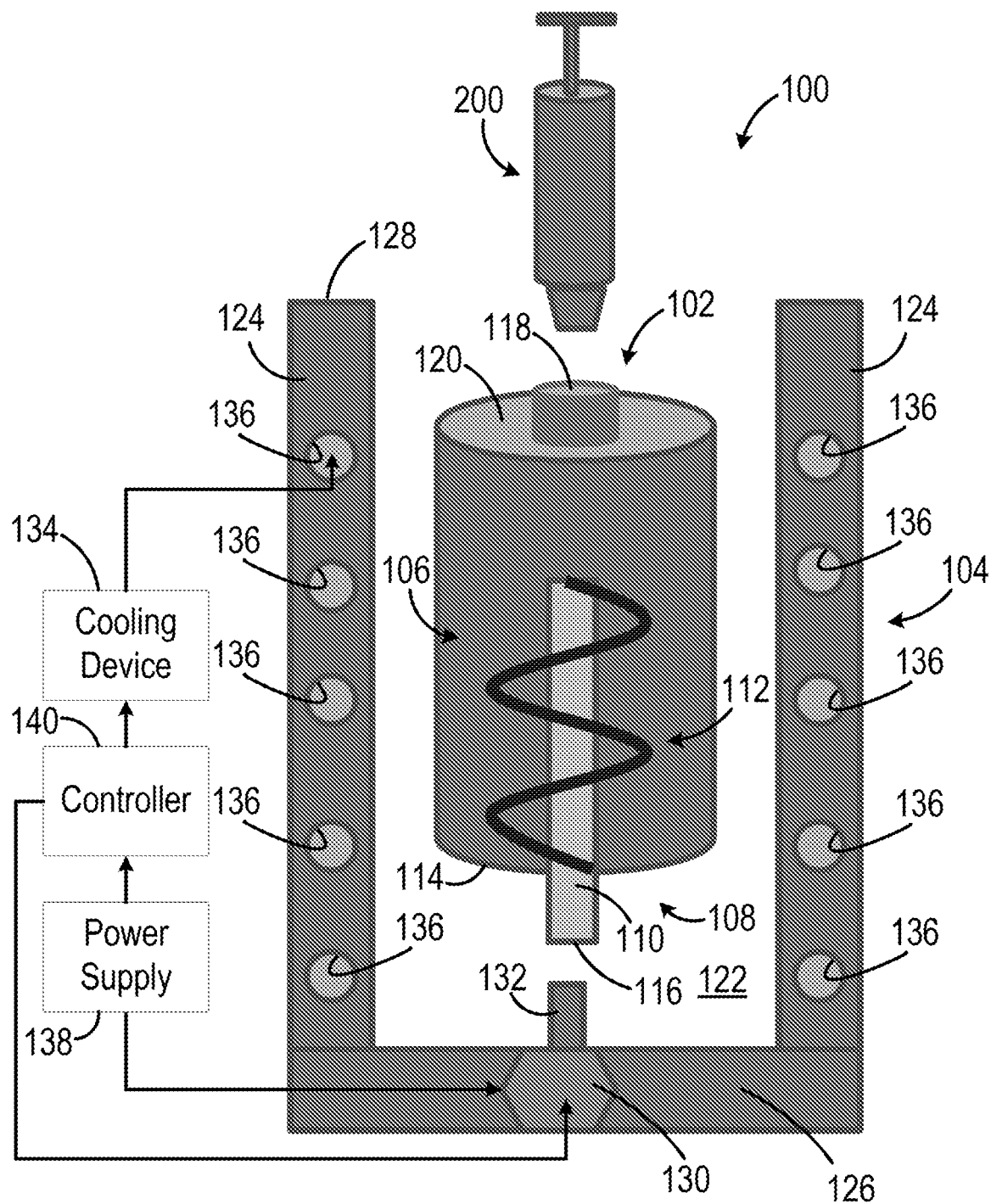
FIG. 4 illustrates the medical ice slurry production system of FIG. 1 with a syringe positioned adjacent to an access port of the medical ice slurry production system.

FIG. 4 illustrates, in one non-limiting example, a sterile extraction syringe 200 configured to be coupled to the access port 118 for withdrawal of the sterile slurry composition 106. In some non-limiting examples, the access port 118 can includes a rubber stopper, a shut off valve, and/or a luer lock with a removable sterile cover. The sterile extraction syringe 200 can include a needle (not shown) to facilitate injection of the sterile slurry composition 106 into the patient. In some non-limiting examples, the needle (not shown) can be 19 gauge or smaller. The agitator 108 can be structured to break up the ice crystals formed in the sterile slurry composition 106 into a size that corresponds with allowing the slurry to flow through a diameter of a needle on the sterile extraction syringe 200. In one non-limiting example, the ice-crystal size can be for example, less than approximately 1 mm or less than approximately −0.3 mm.

Figure 5:
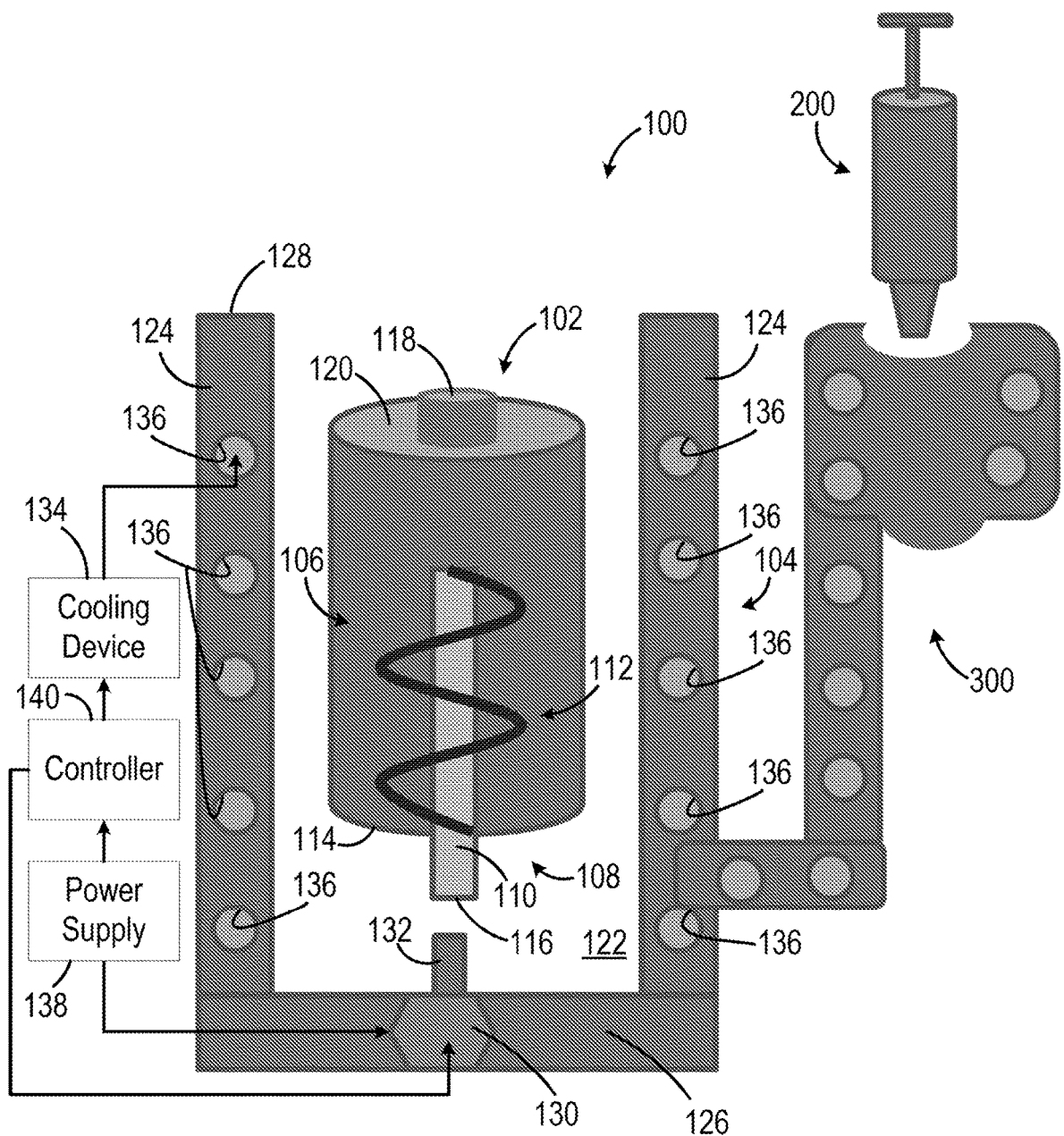
FIG. 5 illustrates the medical ice slurry production system of FIG. 1 with an syringe holder coupled to a housing of the medical ice slurry production system.

Turning to FIG. 5, in some non-limiting examples, the medical ice slurry production system 100 includes a syringe holder 300 coupled to the housing 104. In other non-limiting examples, the syringe holder 300 can be separate from the housing 104. The sterile extraction syringe 200 can be placed within the syringe holder 300 to insulate in the sterile slurry composition 106 within the sterile extraction syringe 200. In some non-limiting examples, the syringe holder 300 is actively cooled, for example, by coupling the syringe holder to the cooling device 134 to maintain the sterile slurry composition 106 within the sterile extraction syringe 200 at the desired slurry temperature. Alternatively or additionally, the syringe holder 300 can include an agitator to prevent separation of the sterile slurry composition 106 within the sterile extraction syringe 200 prior to injection. It should be known that the syringe holder 300 may be integrated into any configurations of the medical ice slurry production system 100 described herein.

Figure 6:
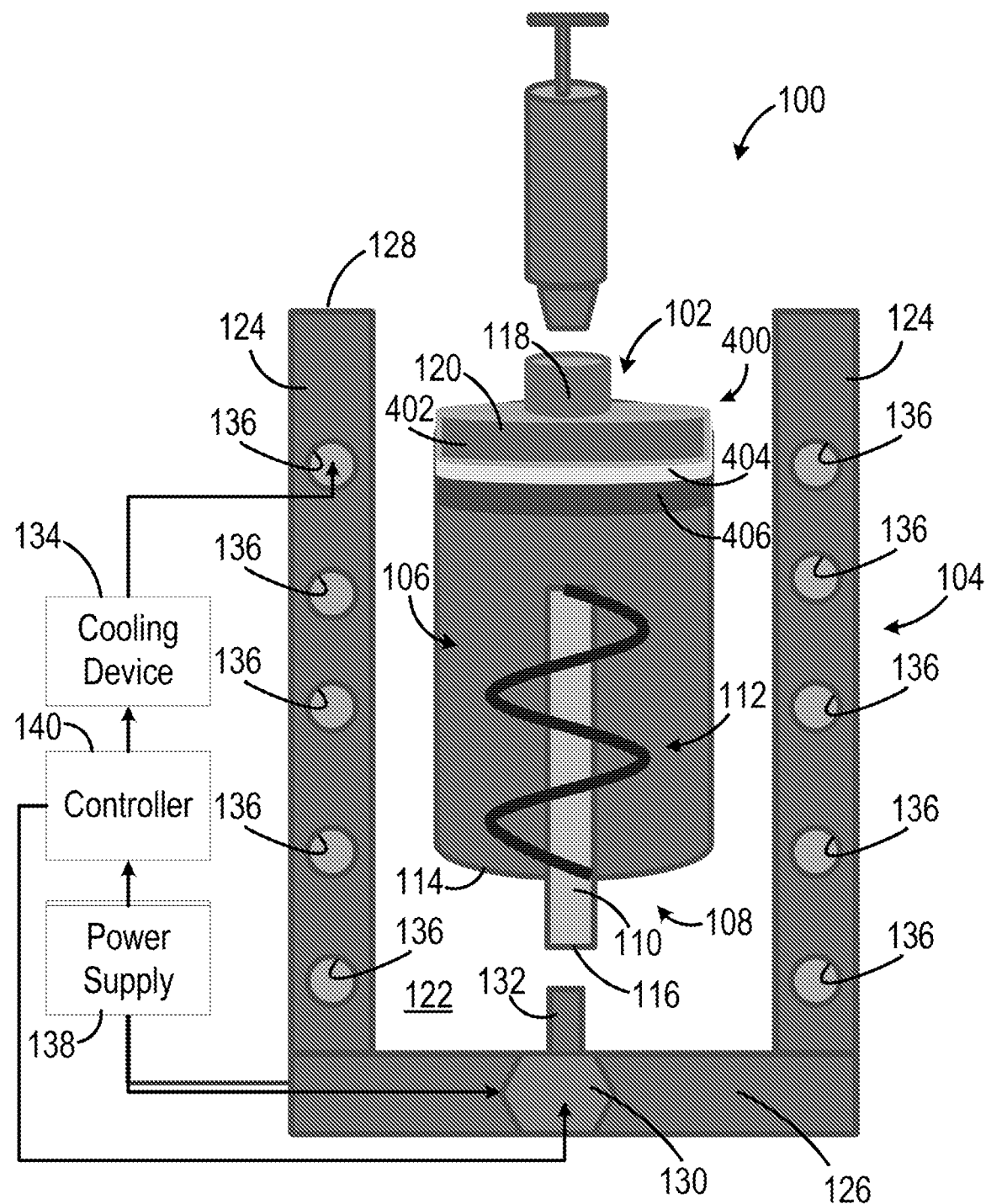
FIG. 6 illustrates the medical ice slurry production system of FIG. 4 with one or more filters arranged within a disposable cartridge of the medical ice slurry production system.

As illustrated in FIG. 6, in some non-limiting examples, the disposable cartridge 102 includes one or more filters 400 arranged adjacent to the access port 118. The one or more filters 400 ensure that ice crystals of a desired size are withdrawn by the sterile extraction syringe 200 and subsequently injected into the patient. In the illustrated non-limiting example, the one or more filters 400 includes a first filter 402, a second filter 404 and a third filter 406 where the second filter 404 is arranged between the first filter 402 and the third filter 406. The first filter 402 is configured to filter ice crystals with a first size. The second filter 404 is configured to filter ice crystals with a second size that is smaller than the first size, and the third filter 406 is configured to filter ice crystals with a third size that is smaller than the second size. As would be recognized by one of skill in the art, the ice crystal size filtered by the first, second, and third filters 402, 404, and 406 can be used to control a size of the ice crystals in the sterile slurry composition 106 injected into the patient. For example, in one non-limiting example, the first size is approximately 500 micrometers (μm), the second size is approximately 250 μm, and the third size is approximately 100 μm. In other non-limiting examples, the disposable cartridge 102 can include any number of filters 400 to filter any size ice crystals, as desired.

Figure 7:
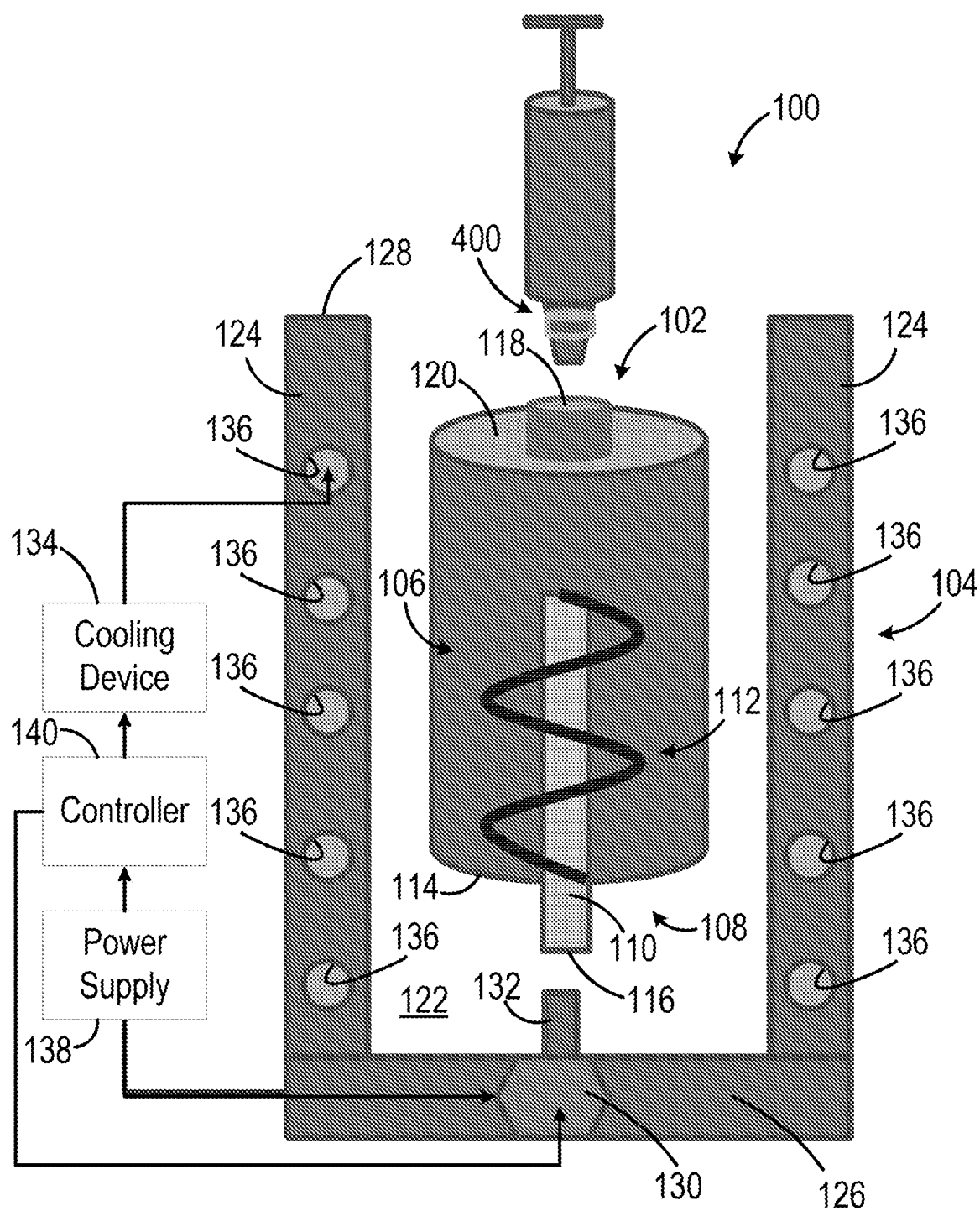
FIG. 7 illustrates the medical ice slurry production system of FIG. 4 with one or more filters arranged within a syringe.

In another non-limiting example, the one or more filters 400 are instead arranged within the sterile extraction syringe 200, as illustrated in FIG. 7.

FIGS. 8-11 illustrate additional non-limiting examples of the agitator 108 of disposable cartridge 102 that are operable with the actuator 130 to break up ice crystals and mix or agitate the sterile slurry composition 106. FIG. 8 illustrates agitator 108 without the fin 112 of FIG. 1. FIG. 9 illustrates agitator 108 including a plurality of ridged protrusions 700 arranged axially along the interior of the disposable cartridge 102. Each ridged protrusion 700 extends toward the agitator shaft 110 and fin 112 coupled thereto. The plurality of ridged protrusions 700 help facilitate the break-up of ice crystals in the sterile slurry composition 106 as well as the mixing of the sterile slurry composition 106.

FIG. 10 illustrates the agitator 108 including a plurality of blades 800 coupled to the agitator shaft 110. Blades 800 includes a plurality of tapered edges to facilitate breaking up the ice crystals and mixing the sterile slurry composition 106. The size of the ice crystals formed by rotating the blades 800 within the sterile slurry composition 106 can be controlled by the degree at which each blade edge is tapered and/or a length of each blade 800. In one non-limiting example, each blade 800 can define a length that is between approximately 12.5% and 99% of a diameter defined by the disposable cartridge.

FIG. 11 illustrates the agitator 108 having a plurality of ridged bladed protrusions 900 arranged axially along the interior of disposable cartridge 102. The plurality of ridged bladed protrusions 900 each extend radially inwards. Here, the agitator shaft 110 is rigidly coupled to the first side 114 of the disposable cartridge 102 to enable the entire disposable cartridge 102 to be agitated in response to rotation or vibration provided by the actuator 130. It should be known that various combinations of one or more of each configuration of agitator 108 illustrated in FIGS. 1 and 8-11 is within the scope of the present disclosure.

Figure 12:
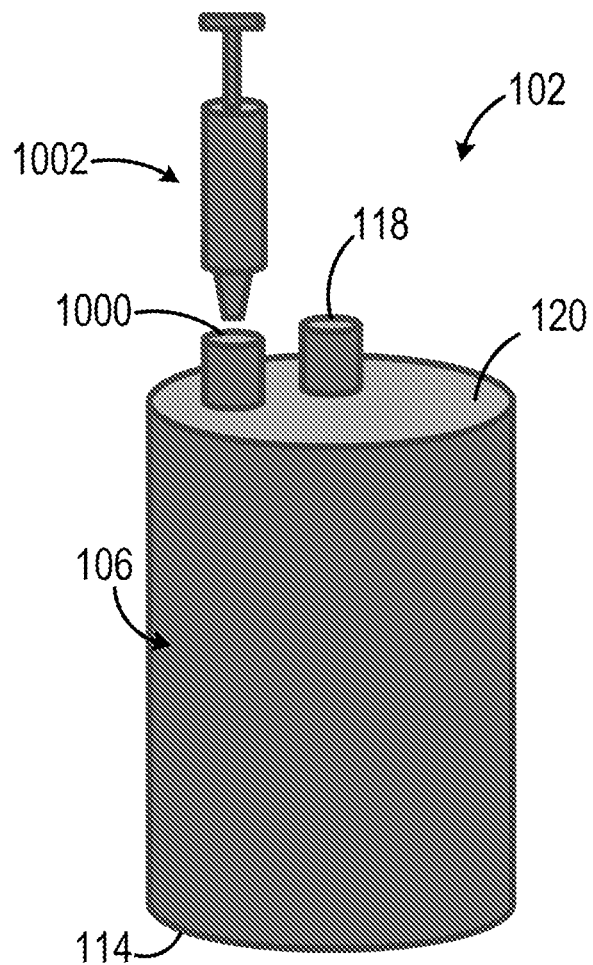
FIG. 12 illustrates a disposable cartridge of the medical ice slurry production system of FIG. 1 with an additive port.

FIG. 12 illustrates another non-limiting example of disposable cartridge 102. As illustrated in FIG. 12, disposable cartridge 102 includes an additive port 1000 arranged in a second side 120 of the disposable cartridge 102. The additive port 1000 is structured and arranged to allow, for example, a therapeutic agent or microbubbles of therapeutic gasses, to be injected into sterile slurry composition 106 within the disposable cartridge 102 by for example an additive syringe 1002. The additive port 1000 can include, for example, a rubber stopper configured to be pierced by a needle, a shut off valve, and/or a luer lock mechanism with a removable sterile cover. Alternatively or additionally, the additive syringe 1002 can be used to inject a thermal agent into the sterile slurry composition 106 to facilitate the cyclical heating and cooling of the sterile slurry composition 106 so as to form smooth ice crystals suitable for injection into a patient.

Figure 13:
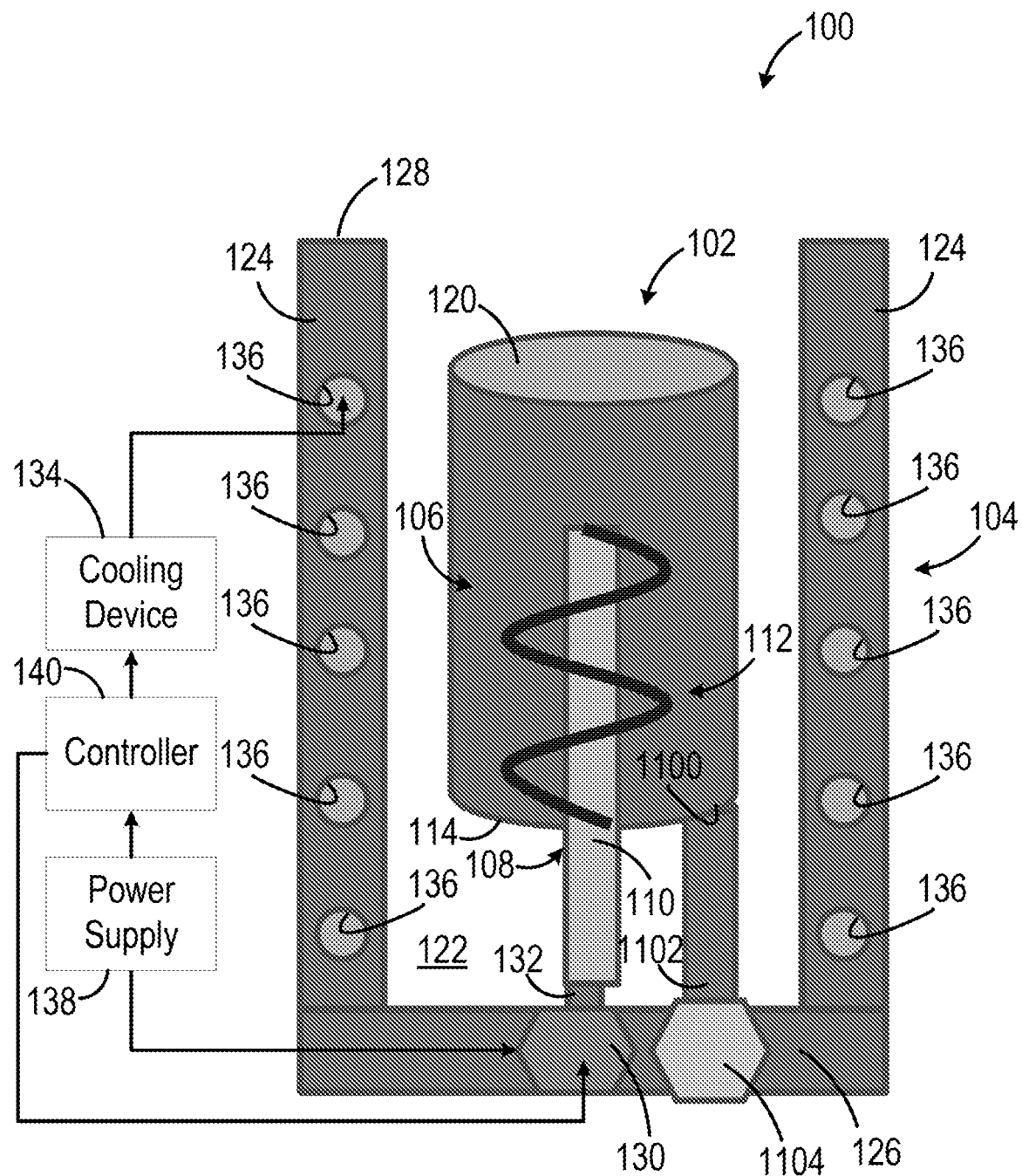
FIG. 13 is a schematic illustration of a medical ice slurry production system according to another non-limiting example of the present disclosure.

FIG. 13 illustrates another non-limiting example of the medical ice slurry production system 100. The medical ice slurry production system 100 of FIG. 13 is similar to the medical ice slurry production system 100 of FIG. 1 except as described below or is apparent from the figures. Like components are identified with similar reference numerals. As illustrated in FIG. 13, the disposable cartridge 102 includes an access port 1100 arranged in the first side 114 of the disposable cartridge 102. The access port 1100 has an extending portion 1102 that fluidly connects the access port 1100 to a pumping device 1104 supported by the housing 104. The illustrated pumping device 1104 integrated into the base 126 of the housing 104 and configured to furnish the sterile slurry composition 106 from the disposable cartridge 102. In other non-limiting examples, the pump device 1104 may be arranged remotely from the housing 104. The pump device 1104 in various examples can include a volumetric infusion pump or another pumping mechanism known in the art. The pump device 1104 can be coupled to the extending portion 1102 using for example, a luer lock connection with sterile removable cap, a rubber stopper configured to be pierced by a needle, and/or a shut off valve. The controller 140 is in communication with the pump device 1104, and is configured to selectively instruct the pump device 1104 to furnish the sterile slurry composition 106 from the disposable cartridge 102 for injection. The controller 140 is further configured to control a flow rate provided by the pump device 1104. In one non-limiting example, the pump device 1104 can be an infusion pump, a membrane pump, a peristaltic pump, a piston pump, a rotary vane pump or any other pump suitable for withdrawing a medical flurry composition from the disposable container. It should also be appreciated that in an alternative embodiment, port 1100 could fluidly communicate directly with another second port defined in the housing or communicate directly with the pump (i.e., without the extending portion 1102).

Figure 14:
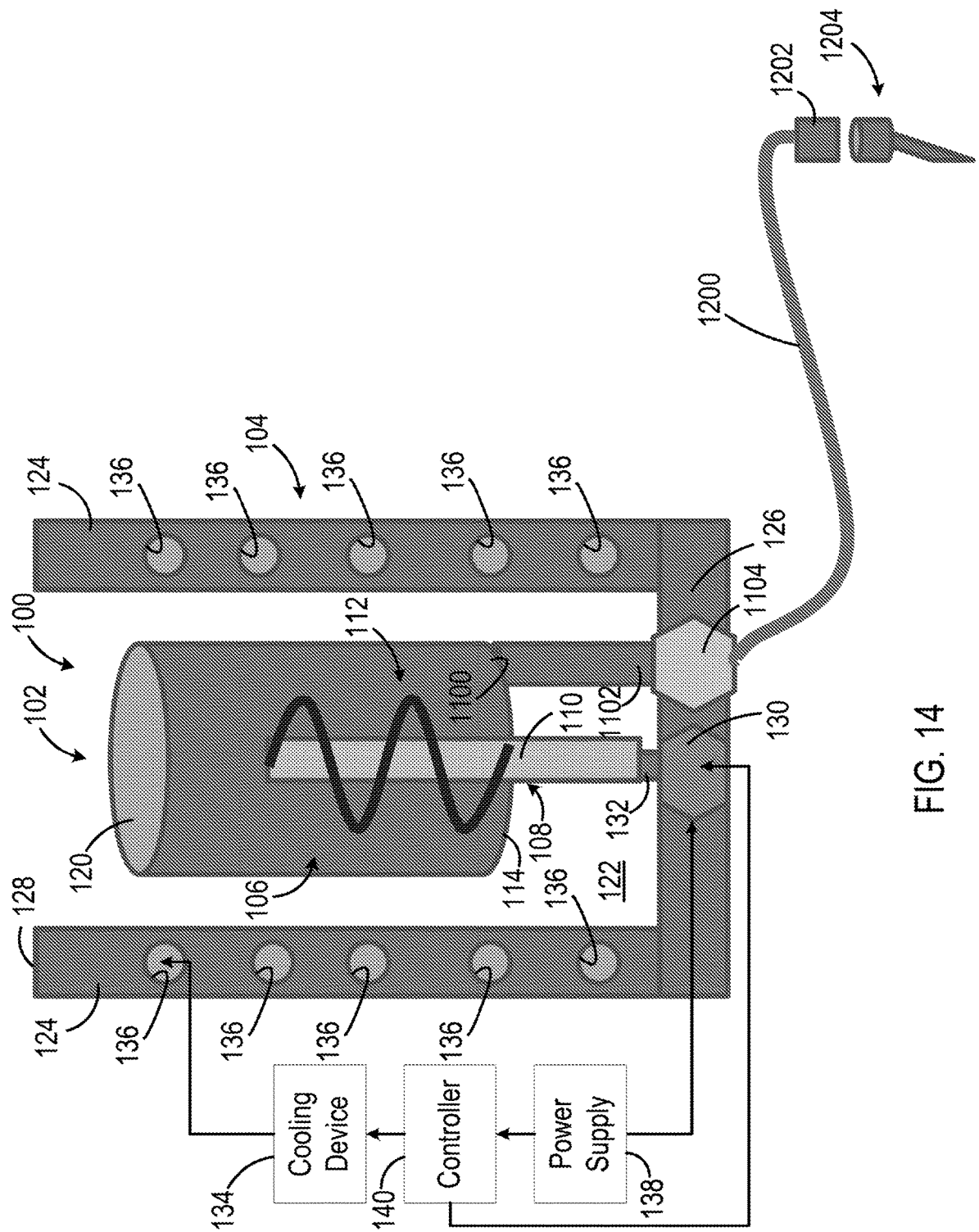
FIG. 14 illustrates the medical ice slurry production system of FIG. 11 with a disposable tube and needle coupled thereto.

FIG. 14 illustrates, in one non-limiting example, the pump device 1104 operating with a disposable tube 1200 and a needle 1204. Needle 1204 can be removably coupled to the disposable tube 1200 via a needle coupling 1202. The disposable tube 1200 can be coupled to the pumping device 1104, for example, using a rubber stopper configured to be pierced by a needle, a luer lock connection with sterile removable cap, and/or a shut off valve. Operation of the medical ice slurry production system 100 of FIGS. 13 and 14 is similar to the medical ice slurry production system 100 of FIG. 1, except as described below or as is apparent from the figures. Once the sterile slurry composition 106 within the disposable cartridge 102 forms ice crystals (due to the composition being cooled to the desired temperature via cooling device 134) and the ice crystals are a desired size (due to the actuation of agitator 108), needle 1204 can be injected into a patient at a treatment location. The controller 140 is then configured to instruct the pump device 1104 to pump the sterile slurry composition 106 into the patient at a desired flow rate for a pre-determined period of time. It should therefore be appreciated that the sterile slurry composition 106 is self-contained throughout the process thereby reducing the burden on an end user to maintain the sterility of the sterile slurry composition 106. Also, the production (i.e., the cooling and forming of the properly sized ice crystals) and delivery (i.e., injection) of the sterile slurry composition 106 for the given medical application is substantially automated by operation of controller 140, cooling device 134, actuator 130, and pump device 1104 together.

Figure 15:
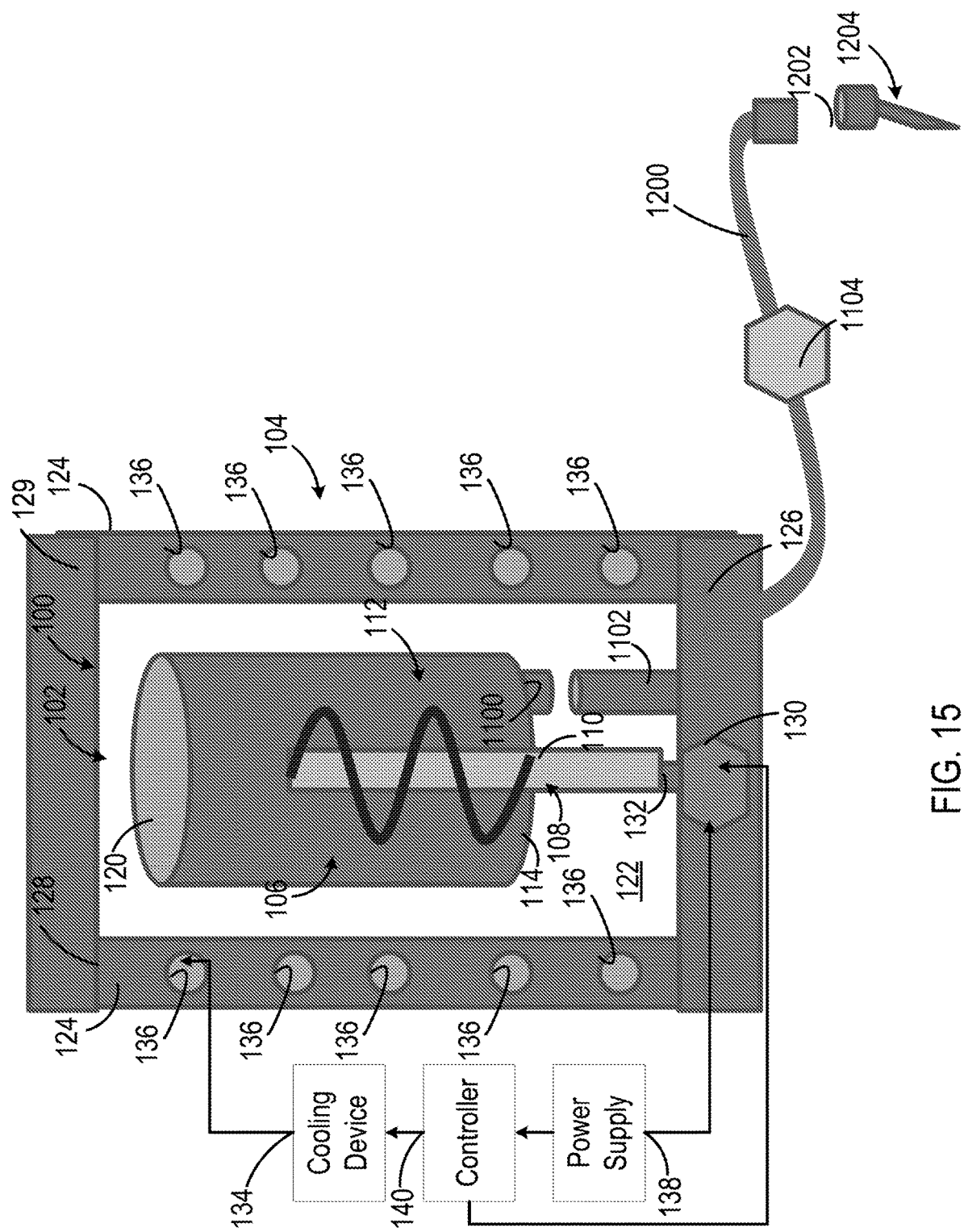
FIG. 15 illustrates the medical ice slurry production system of FIG. 12 with a pump position inline with a disposable tube.

As illustrated in FIG. 15, in another non-limiting example, the pump device 1104 may be arranged inline with the disposable tube 1200 where the disposable tube 1104 threads through the pump device 1104. In this way, the pump device 1104 does not directly contact the pump device 1104.

In certain implementations, pumping devices 1104 can be configured to have a maximum allowable pressure tolerance at the end of the delivery or disposable tube 1200, or at the end of the delivery needle 1204 or a cannula. The pumping devices 1104 can also include adjustable constant-volume pumps, and be configured with user-specified stops that occur when a predefined volume of slurry has been delivered.

FIGS. 16-19 illustrate additional non-limiting examples of the agitator 108 operable with the disposable cartridge 102. The agitator 108 and cartridge 102 illustrated in FIGS. 16-19 are substantially the same as the agitator 108 and cartridge 102 illustrated in FIGS. 8-11 and 13, 14, respectively, except that the extending portion 1102 (of port 1100) in cartridge 102 of FIGS. 16 to 19 extends from a different side of the cartridge 102 towards side wall 124, and is generally horizontally oriented rather than vertically oriented as illustrated in FIGS. 13 and 14.

Figure 20:
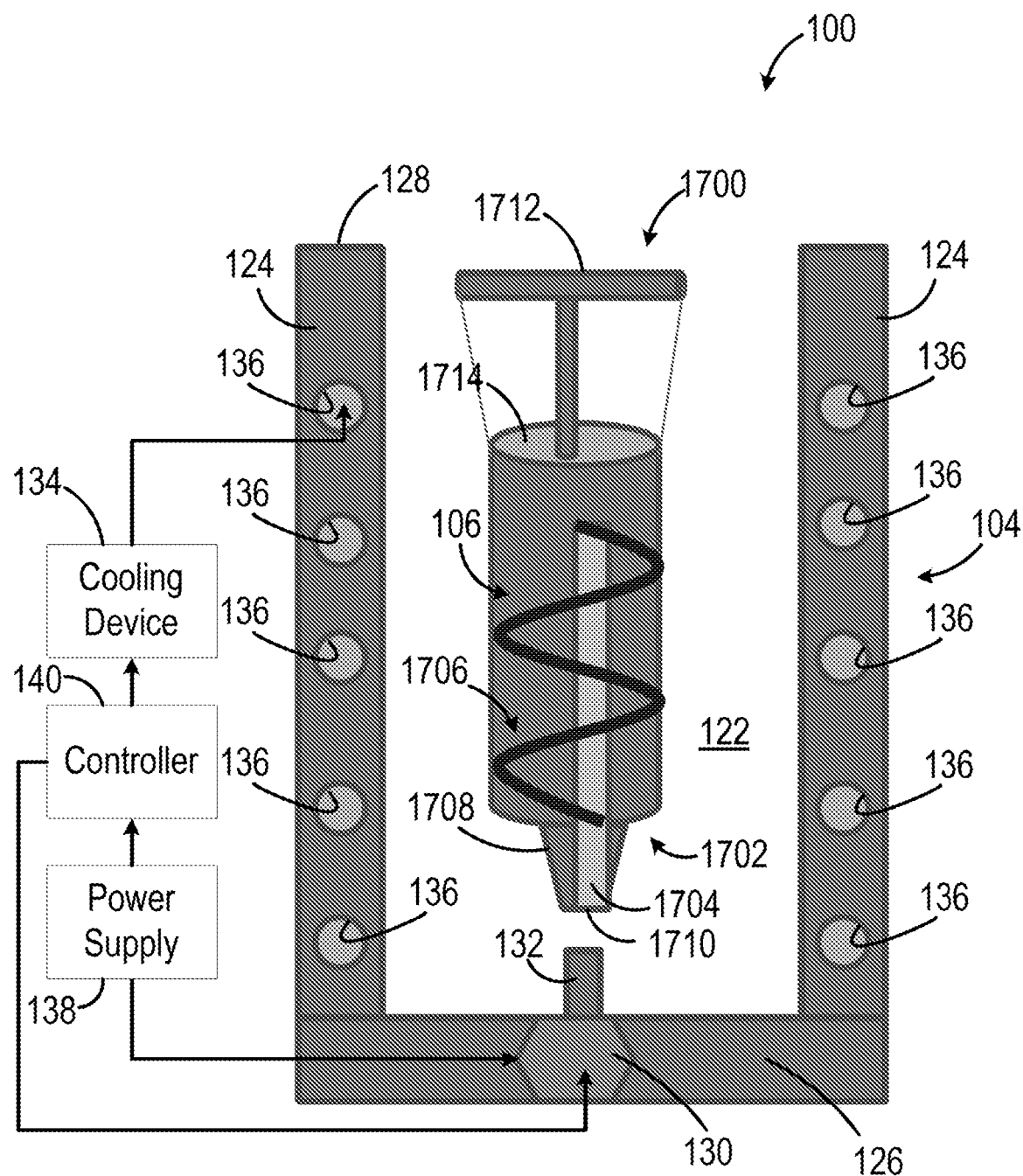
FIG. 20 is a schematic illustration of a medical ice slurry production system according to yet another non-limiting example of the present disclosure.

FIG. 20 illustrates another non-limiting example of the medical ice slurry production system 100. The medical ice slurry production system 100 of FIG. 20 is similar to the medical ice slurry production system 100 of FIG. 1 except as described below or as is apparent from the figures. Like components are identified with similar reference numerals. As illustrated in FIG. 20, the medical ice slurry production system 100 includes a disposable cartridge 1700 configured to be supported within the housing 104. The illustrated disposable cartridge 1700 is in the form of a sterile pre-filled syringe. The disposable cartridge 1700 is pre-filled with the sterile, non-frozen slurry composition 106. Pre-filling the disposable cartridge 1700 with the non-frozen, sterile slurry composition 106 ensures the sterile slurry composition 106 is self contained within a closed environment. This helps relieve an end user's burden of trying to maintain sterility of the slurry composition 106 while handling the disposable cartridge 1700. In some non-limiting examples, the disposable cartridge 1700 may be surrounded by insulation (not shown) to improve thermal stability.

The disposable cartridge 1700 can be fabricated from a plastic, glass, or metal material. The disposable cartridge 1700 can be dimensioned to hold a slurry volume between approximately one cubic centimeter (cc) and approximately one liter (L) depending on the medical application. The illustrated disposable cartridge 1700 is rotationally coupled to the agitator 108. The disposable cartridge 1700 is rotationally coupled to an agitator 1702. The agitator 1702 is similar in operation to the agitator 108 of FIG. 1, described above, except that the agitator 1702 is structured to be operable with disposable cartridge 1700. The agitator 1702 includes a agitator shaft 1704 and a fin 1706 arranged within the disposable cartridge 1700 and coupled to the agitator shaft 1704. Fin 1706 spirals lengthwise along agitator shaft 1704. The agitator shaft 1704 is received within the disposable cartridge 1700. The agitator shaft 1704 is rotationally sealed to a tapered tip 1708 of the disposable cartridge 1700 to allow rotation of the agitator shaft 1704 with respect to the disposable cartridge 1700 while maintaining a seal between the sterile slurry composition 106 and the surrounding environment. The agitator shaft 1704 can be rotationally sealed to the tapered tip 1708, for example, by utilizing, at least one of a sealed hydrostatic, a sealed hydrodynamic, a fluid bearing, and an o-ring.

The disposable cartridge 1700 includes an access port 1710 arranged in a distal end 1712 of the tapered tip 1708 and a plunger 1712. The access port 1710 is structured and arranged to allow the medical ice slurry composition 106 to be injected from the disposable cartridge 1700 and injected into a patient. For example, access port 1710 can be configured for coupling to a needle. The plunger 1712 is slidably received within a second side 1714 of the disposable cartridge 1700 opposite to the tapered tip 1708. The plunger 1712 is configured to displace axially with respect to the disposable cartridge 1700 to inject the sterile slurry composition 106 within the disposable cartridge 1700.

Operation of the medical ice slurry production system 100 of FIG. 20 is similar to the medical ice slurry production system 100 of FIG. 1 except as described below or is apparent from the figures. Once the sterile slurry composition 106 within the disposable cartridge 1700 is cooled to the desired temperature via the cooling device 134, and includes ice crystals of the desired size due to the agitator 1702, the disposable cartridge 1704 is removed from the housing 104 and a needle is coupled to the tapered tip 1708 of the disposable cartridge 1700. Alternatively or additionally, the disposable cartridge 1700 may be placed within a syringe holder similar to the syringe holder 300 of FIG. 5 for safe storage prior to injection. The sterile slurry composition 106 is then injected into a patient at a treatment location. Thus, the sterile slurry composition 106 is self-contained throughout the medical ice slurry production process thereby reducing a clinician's burden of maintaining the sterility of the sterile slurry composition 106 during delivery and production. Again, the production (i.e., the cooling and forming of the properly sized ice crystals) of the sterile slurry composition 106 for the given medical application is substantially automated by operating the controller 140, the cooling device 134, and the actuator 130 together. Using disposable container 1700 to deliver the sterile composition 106 also negates the need to transfer the slurry composition 106 after production.

FIGS. 21-28 illustrate additional non-limiting examples of the agitator 1702 of disposable cartridge 1700 being operable with the actuator 130 to break up ice crystals and mix the sterile slurry composition 106. As illustrated in FIG. 21, the agitator 108 includes a plurality of ridged protrusions 1800 arranged axially along the interior of the disposable cartridge 1700. The plurality of ridged protrusions 1800 each extend towards the agitator shaft 1704 and the fin 1706 coupled thereto. In operation, the rotation of the agitator shaft 1704 and thereby the fin 1706 rotate the fin 1706 past to the plurality of ridged protrusions 1800 to facilitate breaking up ice crystals and mixing the sterile slurry composition 106.

As illustrated in FIG. 22, the agitator 1702 includes a plurality of blades 1900 coupled to the agitator shaft 1704. The blades 1900 include a plurality of tapered edges to facilitate breaking up ice crystals and mixing the sterile slurry composition 106. Blades 800 includes a plurality of tapered edges to facilitate breaking up the ice crystals and mixing the sterile slurry composition 106. The size of the ice crystals formed by rotating the blades 800 within the sterile slurry composition 106 can be controlled by the degree at which each blade edge is tapered and/or a length of each blade 800. In one non-limiting example, each blade 800 can define a length that is between approximately 12.5% and 99% of a diameter defined by the disposable cartridge.

As illustrated in FIG. 23, the agitator 1702 comprises a plurality of ridged bladed protrusions 2000 arranged axially along the interior of the disposable cartridge 1700. The plurality of ridged bladed protrusions 2000 each extend radially inwards. In this non-limiting example, the agitator 1702 includes a cap 2002 that is configured to rigidly couple the tapered tip 1708 of the disposable cartridge 1700 and the actuator 130 to enable the entire disposable cartridge 1700 to be agitated in response to rotation and/or vibration provided by the actuator 130.

As illustrated in FIG. 24, the agitator 1702 includes a plurality of particles 2100 pre-filled in the disposable cartridge 1700 along with the sterile slurry composition 106. In this non-limiting example, the disposable cartridge 1700 is operable with the cap 2002, and the plurality of particles 2100 facilitate turbulent mixing and agitation within the disposable cartridge 1700 in response to rotation and/or vibration provided by the actuator 130. As illustrated in FIG. 25, the agitator 1702 comprises a plurality of blades 2200. Each of the plurality of blades 2200 includes a plurality of tapered edges to facilitate breaking up ice crystals and mixing the sterile slurry composition 106. A degree of the taper defined by the tapered edges and/or a length defined by each of the plurality of blades 2200 can control a size of the ice crystals formed by rotating the plurality of blades 2200 within the sterile slurry composition 106. In one non-limiting example, the plurality of blades 2200 can define a length that is between approximately 12.5% and 99% of a diameter defined by the disposable cartridge. Additionally, each of the plurality of blades 2200 can be configured to counter-rotate with respect to one another.

As illustrated in FIG. 26, the agitator 1702 includes a paddle 2300 coupled to the agitator shaft 1704 for rotation therewith. As illustrated in FIG. 27, the agitator 1702 includes the paddle 2300 and a plurality of fins 2400 coupled to an interior surface of the paddle 2300. As illustrated in FIG. 28, the agitator 1702 includes a whisk 2500 coupled to the agitator shaft 1704 for rotation therewith. It should be known that various combinations of the configurations of the agitators 1702 illustrated in FIGS. 20-28 are within the scope of the present disclosure.

Figure 29:
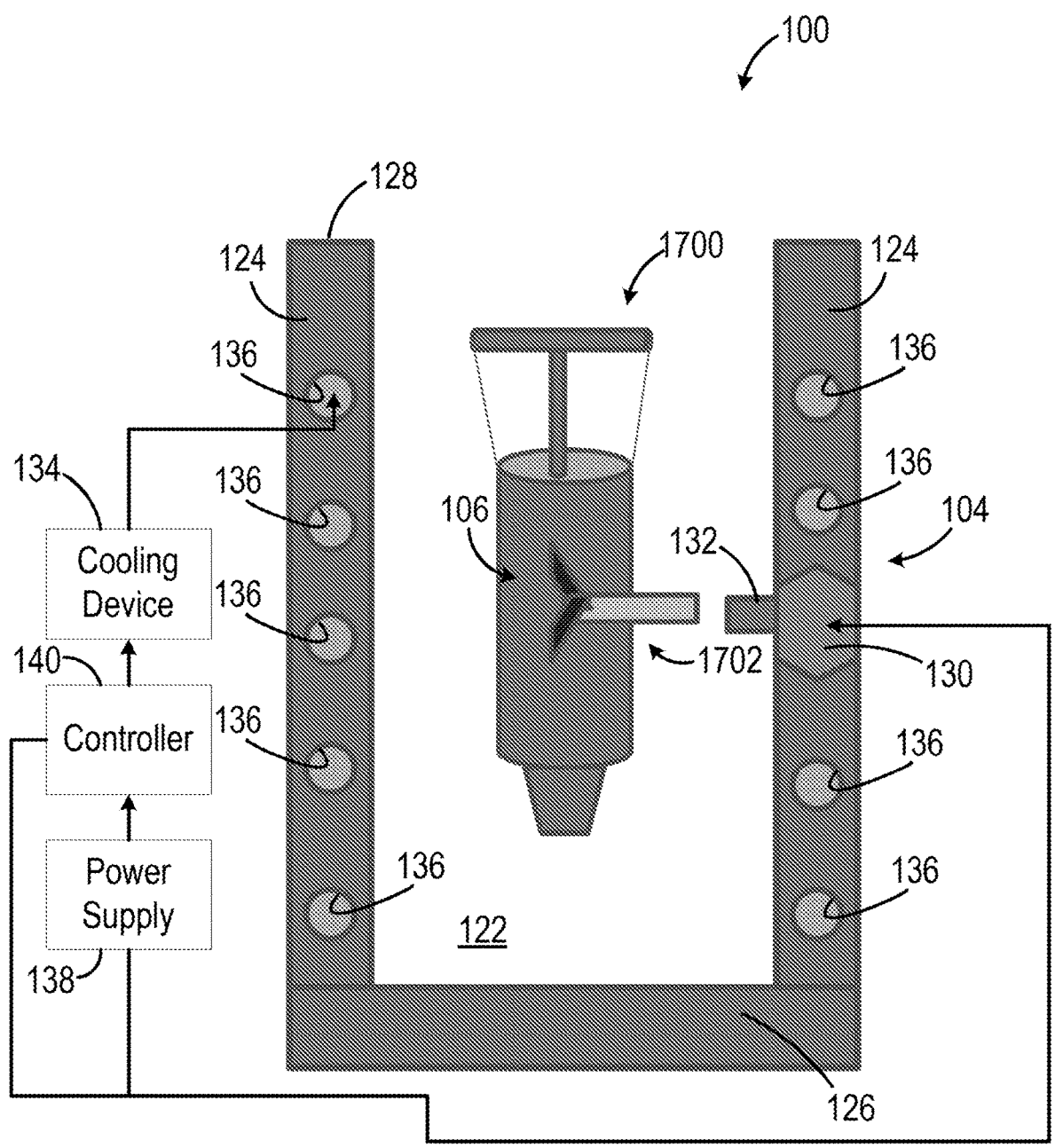
FIG. 29 illustrates the medical ice slurry production system of FIG. 20 with a disposable cartridge having an agitator arranged on a side thereof.

As illustrated in FIG. 29, in one non-limiting example, the agitator 1702 is arranged on a side of the disposable cartridge 1700. In particular, the agitator shaft 1704 protrudes from a side of the disposable cartridge 1700 and includes a blade 1900 coupled to the agitator shaft 1704. It should be appreciated that, in this arrangement, the agitator 1702 may be in the form of any of the configurations of the agitator 1702 described herein. To correspond with this arrangement of the agitator 1702, the actuator 130 is arranged within a corresponding one of the side walls 124 of the housing 104. The actuator shaft 132 protrudes from the corresponding side wall 124 towards the agitator shaft 1704.

Figure 30:
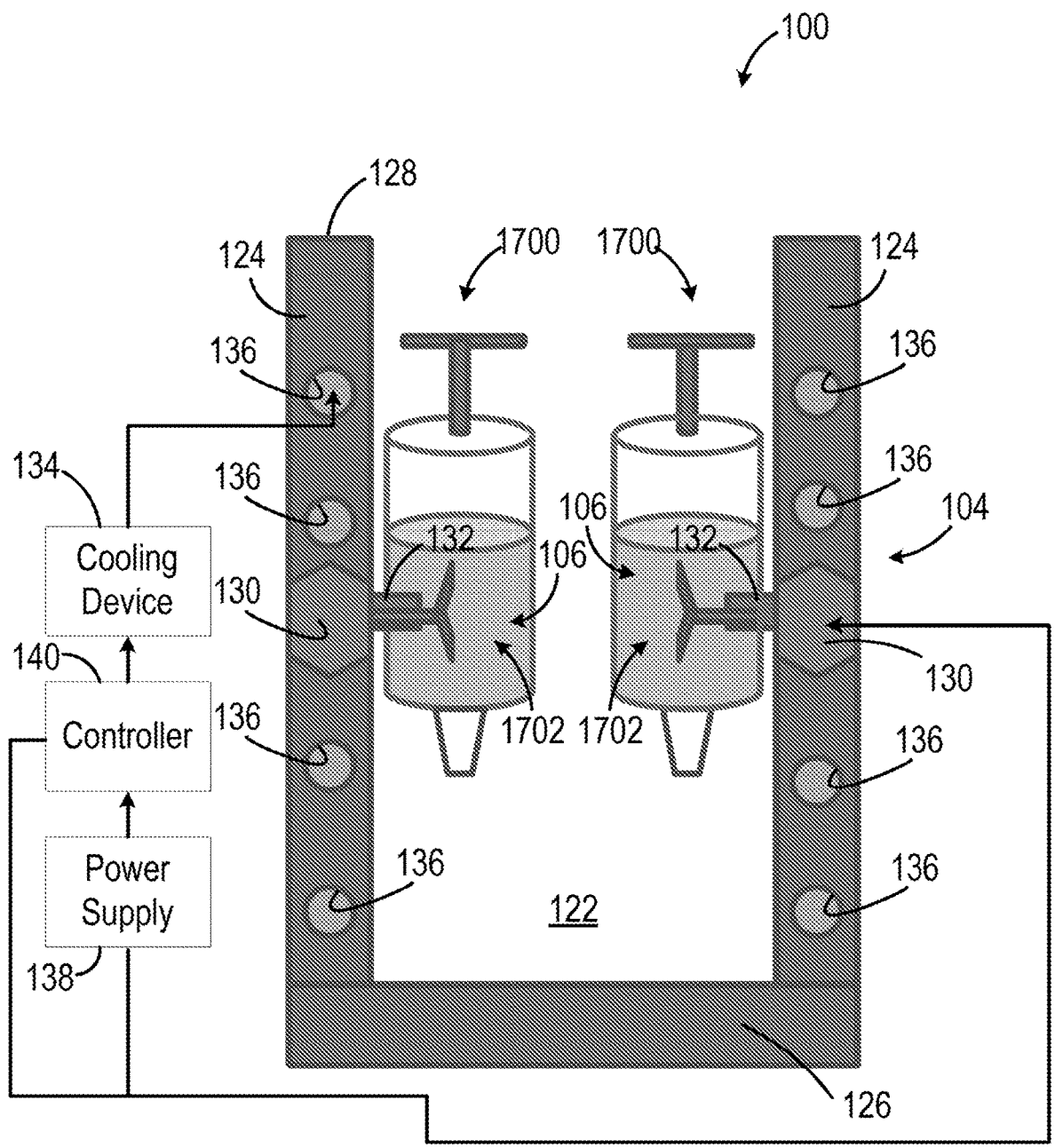
FIG. 30 illustrates the medical ice slurry production system of FIG. 20 with more than one disposable cartridges having agitators on a side thereof.

In another non-limiting example, each of the side walls 124 of the housing 104 may include a corresponding actuator 130 and actuator shaft 132, as illustrated in FIG. 30. This can enable the housing 104 to support a plurality of disposable cartridges 1700 and thereby produce a plurality of sterile slurry compositions 106 for injection into a patient.

As illustrated in FIG. 31, in another non-limiting example where the agitator 1702 is arranged on a side of the disposable cartridge 1700, the agitator 1702 may include a plurality of blades 2800 each configured to counter-rotate with respect to each other.

As illustrated in FIG. 32, in some non-limiting examples, the disposable cartridge 1700 includes one or more filters 2900 arranged adjacent to the access port 1710. The one or more filters 2900 ensure that ice crystals of a desired size are injected by the disposable cartridge 1700. In the illustrated non-limiting example, the one or more filters 2900 include a first filter 2902, a second filter 2904 and a third filter 2906, where the second filter 2904 is arranged between the first filter 2902 and the third filter 2906. The first filter 2902 is configured to filter ice crystals with a first size. The second filter 2904 is configured to filter ice crystals with a second size that is smaller than the first size, and the third filter 2906 is configured to filter ice crystals with a third size that is smaller than the second size. As would be recognized by one of ordinary skill in the art, the ice crystal size filtered by the first, second, and third filters 2902, 2904, and 2906 can be used to control a size of the ice crystals in the sterile slurry composition 106 injected into the patient. For example, in one non-limiting example, the first size is approximately 500 micrometers (μm), the second size is approximately 250 μm, and the third size is approximately 100 μm. In other non-limiting examples, the disposable cartridge 102 can include any number of filters 400 to filter any size ice crystals, as desired.

FIG. 33 illustrates another non-limiting example of the disposable cartridge 1700. As illustrated in FIG. 33, the disposable cartridge 1700 includes an additive port 3000 arranged in a side of the disposable cartridge 1700. The additive port 3000 is structured and arranged to allow an additive syringe 3002 to inject, for example, a therapeutic agent, into sterile slurry composition 106 within the disposable cartridge 1700. The access port 3000 can include, for example, a rubber stopper configured to be pierced by a needle, a luer lock connection with sterile removable cap, and/or a shut off valve. Alternatively or additionally, the additive syringe 3002 can be used to inject a thermal agent into the sterile slurry composition 106 to facilitate the cyclic heating and cooling of the sterile slurry composition 106 needed to form smooth ice crystals.

Figure 34:
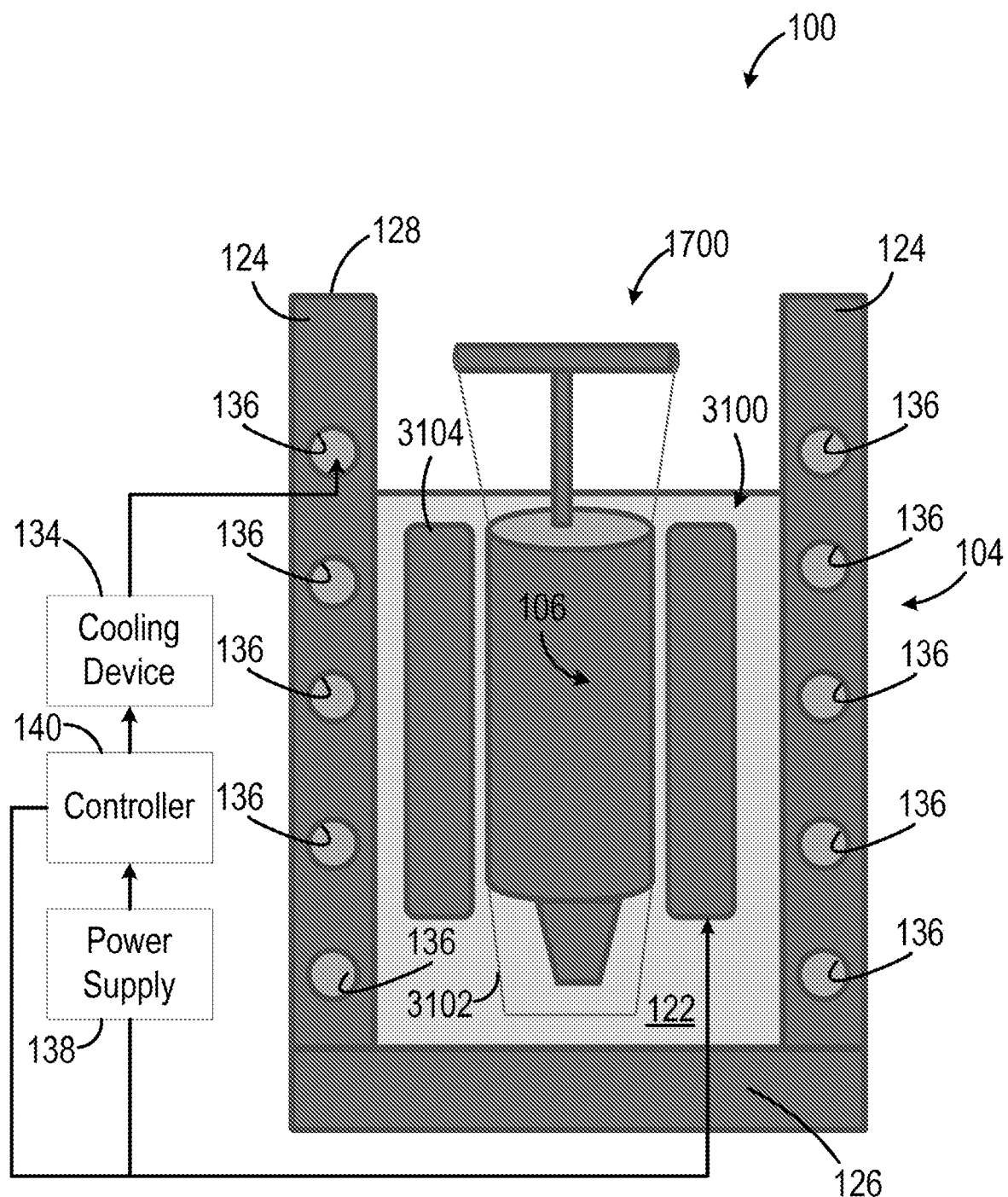
FIG. 34 is a schematic illustration of a medical ice slurry production system according to another non-limiting example of the present disclosure.

FIG. 34 illustrates another non-limiting example of the medical ice slurry production system 100. The medical ice slurry production system 100 of FIG. 31 is similar to the medical ice slurry production systems 100 of FIGS. 1 and 20 except as described below or as is apparent from the figures. Like components are identified with similar reference numerals. As illustrated in FIG. 34, the medical ice slurry production system 100 includes an agitator 3100 in the form of a liquid (e.g., exalcohol, isopropenyl, or ethanol) supported within the internal cavity 122 of the housing 104. The disposable cartridge 1700 is suspended in the agitator 3100 and includes a cap 3102 configured to provide a seal between the access port 1710 and the surrounding agitator 3100. An actuator 3104 in the form of an ultrasonic transducer is arranged around the disposable cartridge 1700. The actuator 3104 is configured to vibrate at an ultrasonic frequency. Ultrasonic waves generated by the actuator 3104 are transferred to the disposable cartridge 1700 by the agitator 3104 to facilitate the breaking of ice crystals formed in the sterile slurry formulation 106 into a desired ice crystal size. The controller 140 is in electrical communication with the actuator 3104 and configured to selectively instruct the actuator 3104 to generate ultrasonic waves carried by the agitator 3100. In operation, the controller 140 is configured to instruct the actuator 3104 to impart ultrasonic waves through the agitator 3100 until the ice crystals in the sterile slurry composition 106 define a desired size. In one non-limiting example, a length of time that the actuator 3104 imparts ultrasonic waves upon the disposable cartridge 1700 can be input to the controller 140. Alternatively or additionally, the controller 140 can be configured to vary a vibration frequency of the actuator 3104 to control a size of the ice crystals within the sterile slurry composition 106.

Figure 35:
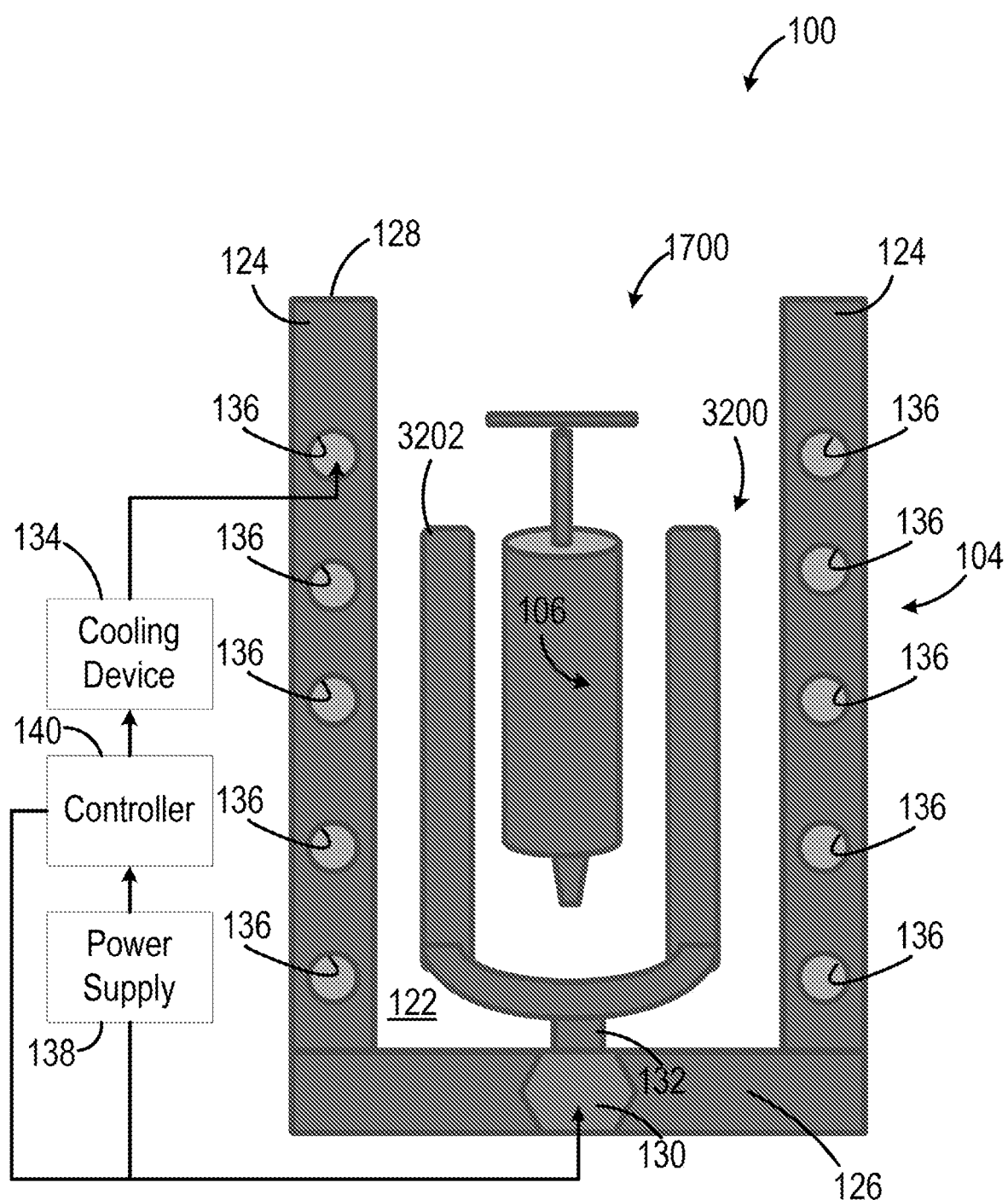
FIG. 35 is a schematic illustration of a medical ice slurry production system according to yet another non-limiting example of the present disclosure.

FIG. 35 illustrates another non-limiting example of the medical ice slurry production system 100. The medical ice slurry production system 100 of FIG. 35 is similar to the medical ice slurry production systems 100 of FIGS. 1 and 20 except as described below or as is apparent from the figures. Like components are identified with similar reference numerals. As illustrated in FIG. 35, the medical ice slurry production system 100 includes an agitator 3200 having a mechanical linkage 3202 supported within the internal cavity 122 of the housing 104. The mechanical linkage 3202 is configured to removably couple the disposable cartridge 1700 to the linkage. Mechanical linkage 3202 of agitator 3200 is coupled to actuator shaft 132 of the actuator 130 to facilitate rotation and/or vibration of the mechanical linkage 3202 and thereby the disposable cartridge 1700. In operation, an end user places the disposable cartridge 1700 within the internal cavity 122 of the housing 104 such that the disposable cartridge 1700 is coupled to the mechanical linkage 3202. The mechanical linkage 3202 is rotated and/or vibrated by the actuator 130 to break up ice crystals formed during production of the sterile slurry composition 106 prior to injection.

Figure 36:
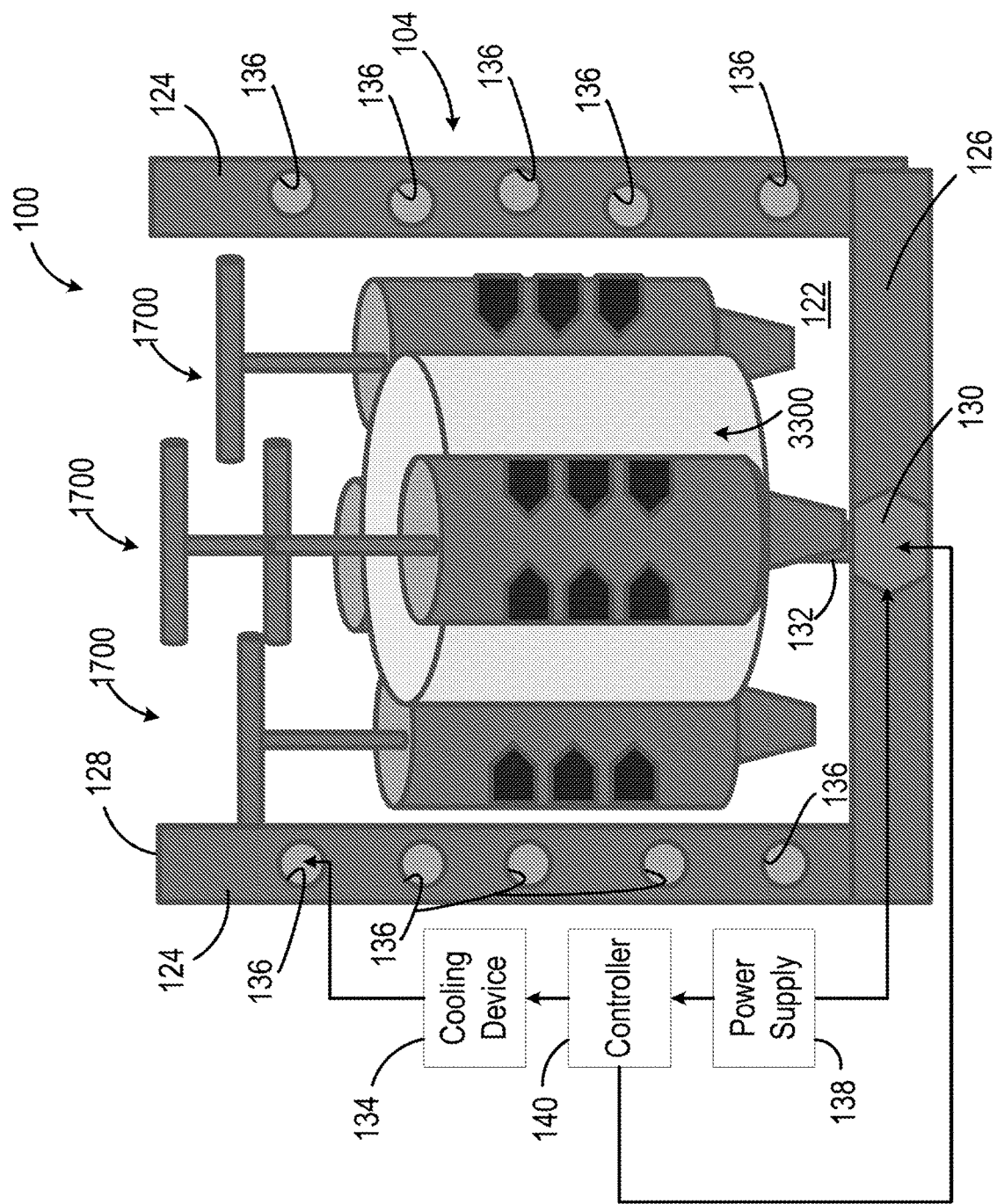
FIG. 36 is a schematic illustration of a medical ice slurry production system according to still another non-limiting example of the present disclosure.

FIG. 36 illustrates another non-limiting example of the medical ice slurry production system 100. The medical ice slurry production system 100 of FIG. 33 is similar to the medical ice slurry production systems 100 of FIGS. 1 and 20 except as described below or is apparent from the figures. Like components are identified with similar reference numerals. As illustrated in FIG. 36, the medical ice slurry production system 100 includes a cartridge support 3300 that defines a generally cylindrical shape. The cartridge support 3300 is configured to removably couple to one or more disposable cartridges 1700. The cartridge support 3300 is coupled to the actuator shaft 132 of the actuator 130 to facilitate movement and/or rotation of the cartridge support 3300 in one or more of an x-direction, a y-direction, and a z-direction. The illustrated disposable cartridges 1700 includes the agitator 1702 having the plurality of ridged bladed protrusions 2000 arranged axially along the interior of the disposable cartridge 1700, as shown in FIG. 23. It should be appreciated that alternative configurations of agitation described herein may be implemented in this non-limiting example.

The movement imparted on the agitator by the actuator 130 and thereby the disposable cartridge 1700 breaks up the ice crystals formed in the sterile slurry composition 106 prior to injection. It would be appreciated that in order to properly balance the agitator 3300 during movement, the disposable cartridges 1700 should be coupled to the agitator 3300 in opposing pairs.

Figure 37:
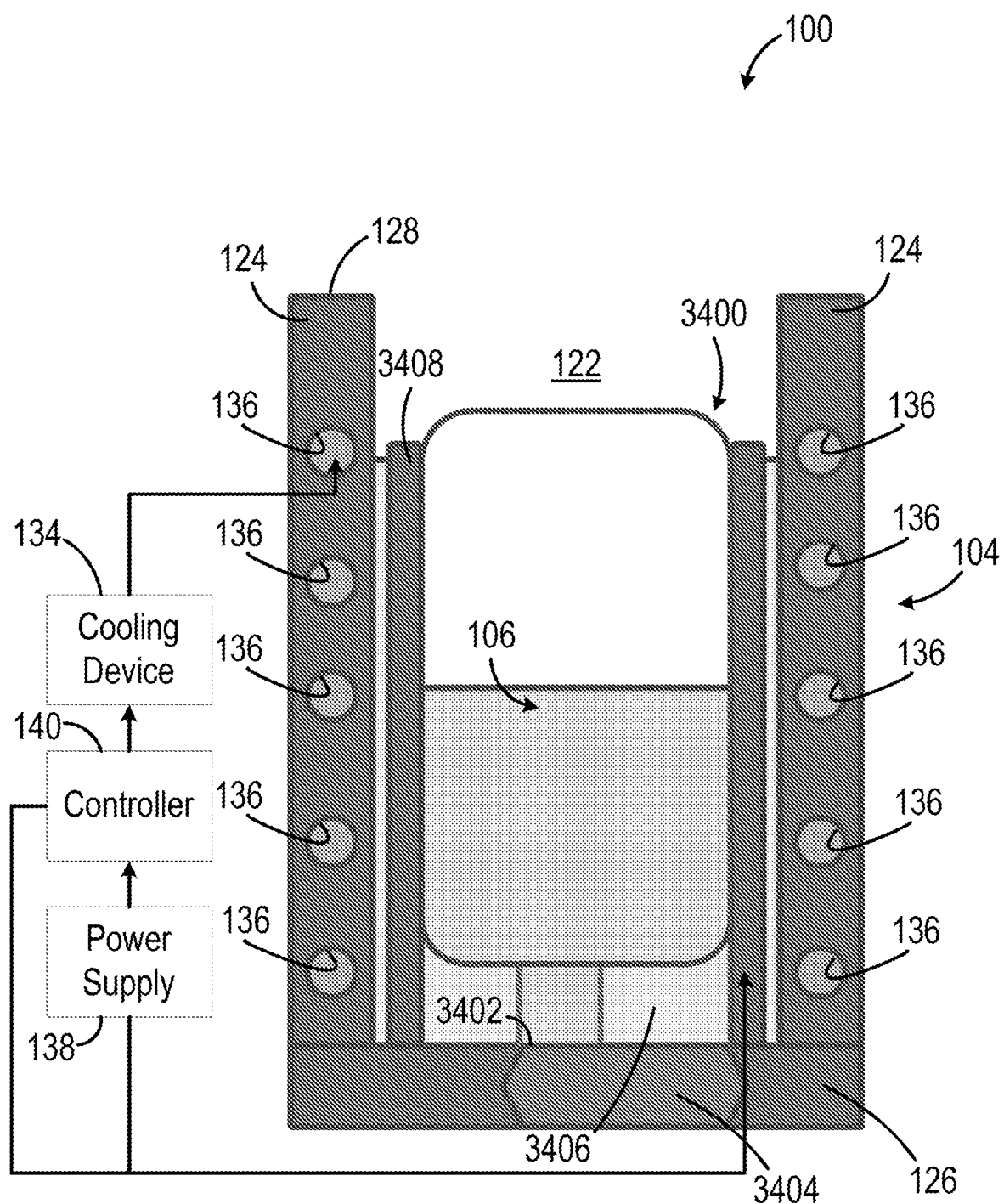
FIG. 37 is a schematic illustration of a medical ice slurry production system according to still another non-limiting example of the present disclosure.

FIG. 37 illustrates another non-limiting example of the medical ice slurry production system 100. The medical ice slurry production system 100 of FIG. 37 is similar to the medical ice slurry production system 100 of FIG. 1 except as described below or is apparent from the figures. Like components are identified with similar reference numerals. As illustrated in FIG. 37, the medical ice slurry production system 100 includes a disposable cartridge 3400 configured to be supported within the housing 104. The illustrated disposable cartridge 3400 is in the form of a sterile pre-filled compressible bag. In some non-limiting examples, the disposable cartridge 3400 is an intravenous (IV) bag. The disposable cartridge 3400 is pre-filled with the sterile slurry composition 106. Pre-filling the disposable cartridge 3400 with the sterile slurry composition 106 ensures the sterile slurry composition 106 is self contained within a closed environment. This helps relieve an end user's burden of trying to maintain sterility of the slurry composition 106 while handling the disposable cartridge 3400. In some non-limiting examples, the disposable cartridge 3400 may be surrounded by insulation (not shown) to improve thermal stability.

The disposable cartridge 3400 can be dimensioned to hold a slurry volume between approximately one cubic centimeter (cc) and approximately one liter (L) depending on the medical application. The illustrated disposable cartridge 3400 includes an access port 3402 fluidly coupled to a pump device 3404. The pump device 3404 is similar in configuration and operation to the pump device 1104 of FIG. 13. That is, the controller 140 is in communication with the pump device 3404 and is configured to selectively instruct the pump device 3404 to pump the sterile slurry composition 106 from the disposable cartridge 3400 for injection. The controller 140 is further configured to control a flow rate provided by the pump device 3404. In one non-limiting example, the pump device 3404 can be an infusion pump or any other pump described herein. Additionally, the pump device 3402 can be coupled to a disposable tube and needle to enable injection into a patient, as shown in FIG. 14.

In certain implementations, pumping device 3404, like pumping device 1104, can be configured to have a maximum allowable pressure tolerance at the end of a delivery or disposable tube, or at the end of a delivery needle or cannula. The pumping devices 3404 can also include adjustable constant-volume pumps, and be configured with user-specified stops that occur when a predefined volume of slurry has been delivered.

The illustrated agitator 3406 and actuator 3408 are similar to the agitator 3100 and 3104 of FIG. 34. That is, the actuator 3408 is configured to produce ultrasonic vibrations that are carried through the agitator 3406 to the disposable container 3400 to break up the ice crystals in the sterile slurry composition 106 prior to injection.

Figure 38:
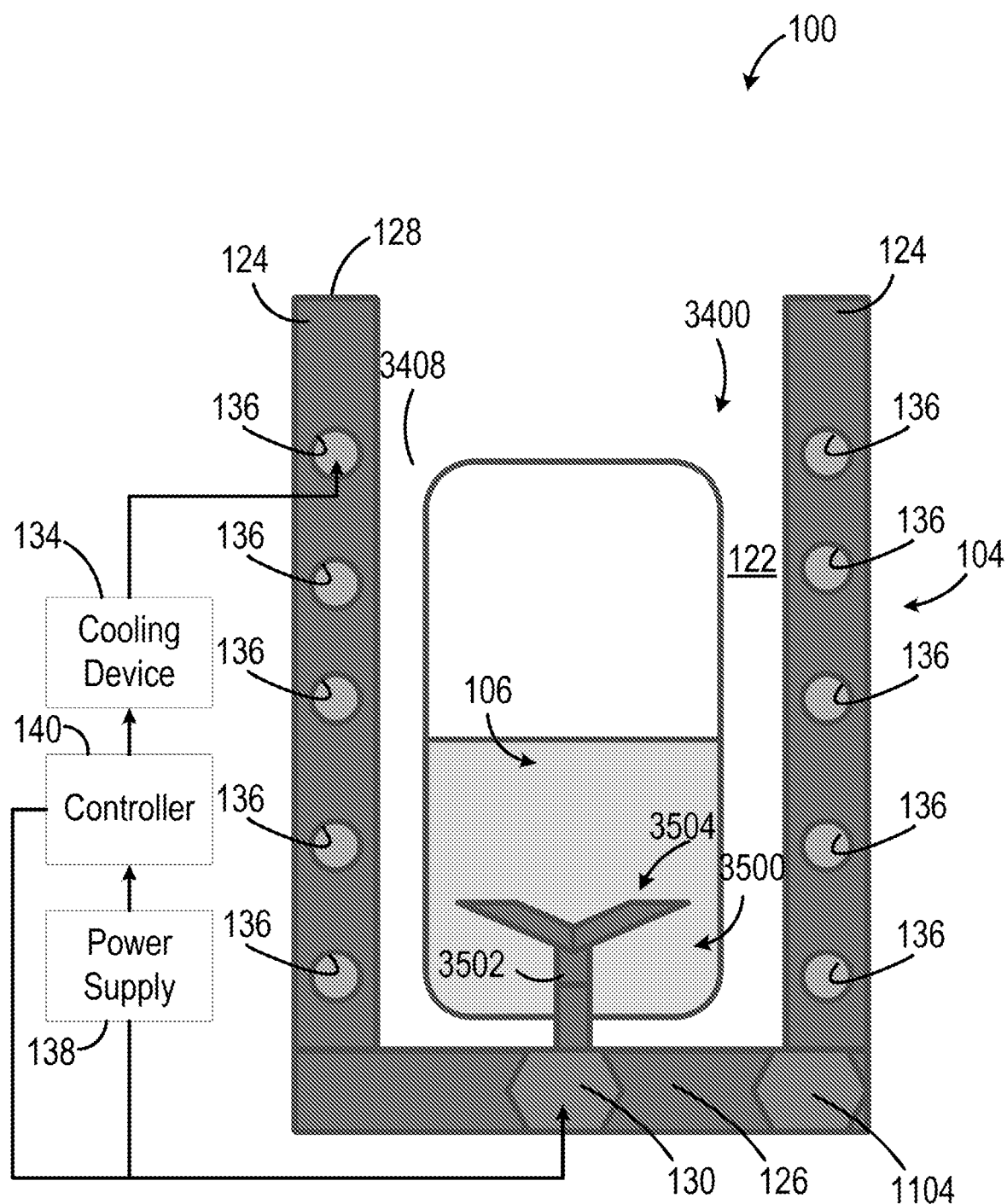
FIG. 38 illustrates the medical ice slurry production system of FIG. 37 with another non-limiting example of an agitator.

As illustrated in FIG. 38, in another non-limiting example, the disposable cartridge 3400 is coupled to an agitator 3500. The agitator 3500 includes an agitator shaft 3502 coupled to a plurality of blades 3504 arranged within the disposable cartridge 3400. The agitator shaft 3502 is coupled to the actuator shaft 132 to enable the blades 3504 to rotate within the disposable cartridge 3400 and break up ice crystals formed in the sterile slurry composition 106 to a desired size.

Figure 39:
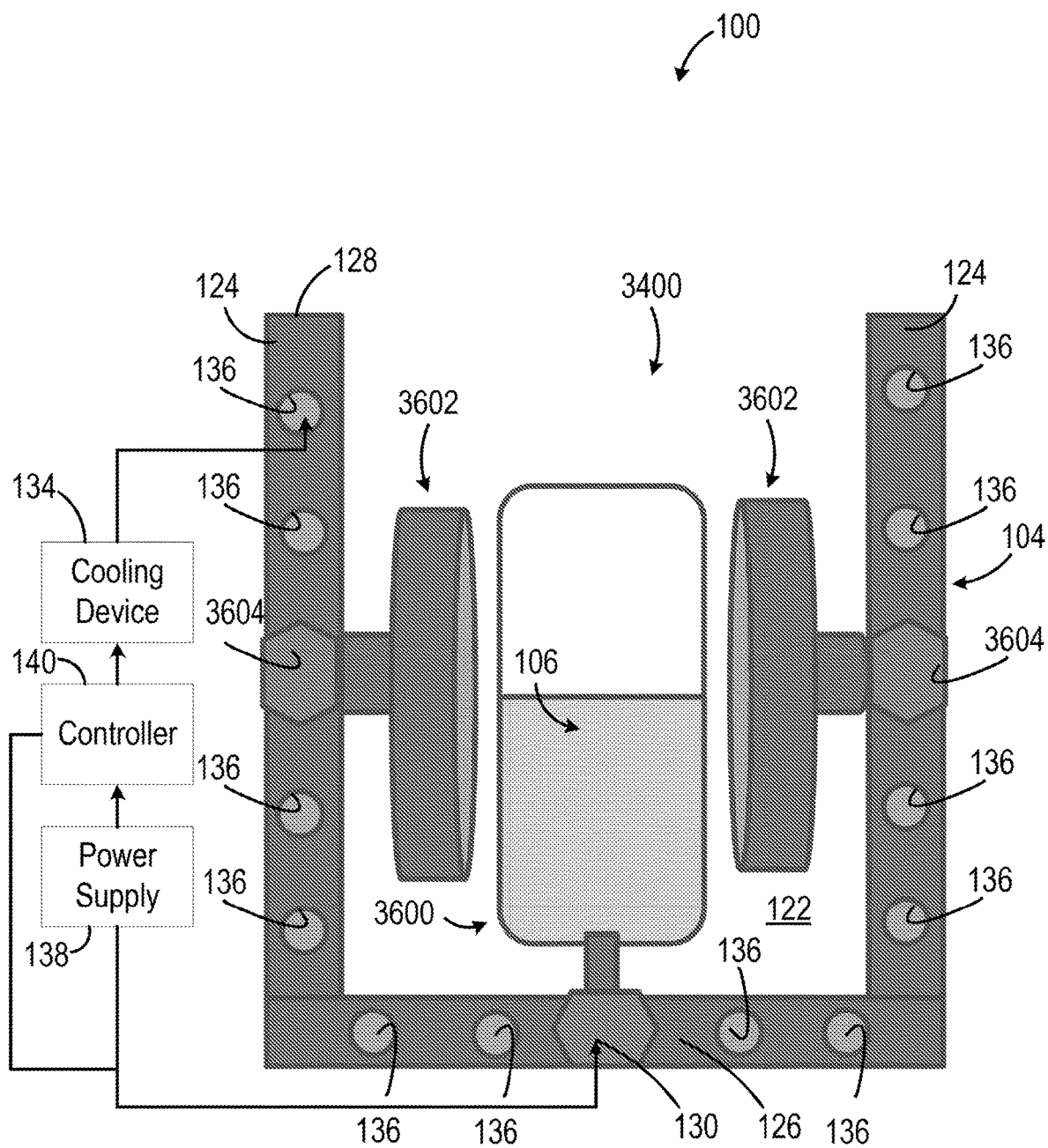
FIG. 39 illustrates the medical ice slurry production system of FIG. 37 with still another non-limiting example of an agitator.

In yet another non-limiting example, the disposable cartridge 3400 is operable with an agitator 3600, as illustrated in FIG. 39. The agitator 3600 includes a pair of opposing supports 3602 each coupled to an actuator 3604 arranged in a corresponding one of the side walls 124 of the housing 104. The pair of opposing supports 3202 are each configured to be movable to compress the disposable cartridge 3400 and to supply agitation to break up ice crystals formed in the sterile slurry composition 106. In operation, the controller 140 is configured to apply agitation to the disposable cartridge 3400 via one or more agitators 3606 coupled to the actuators 3604. Once the sterile slurry composition 106 reaches the desired temperature and includes ice crystals of the desired size, the controller 140 is configured to instruct the actuators 3604 to displace to compress the disposable cartridge 3400 and thereby force the sterile slurry composition 106 through the access port 3402 for injection into the patient.

Figure 40:
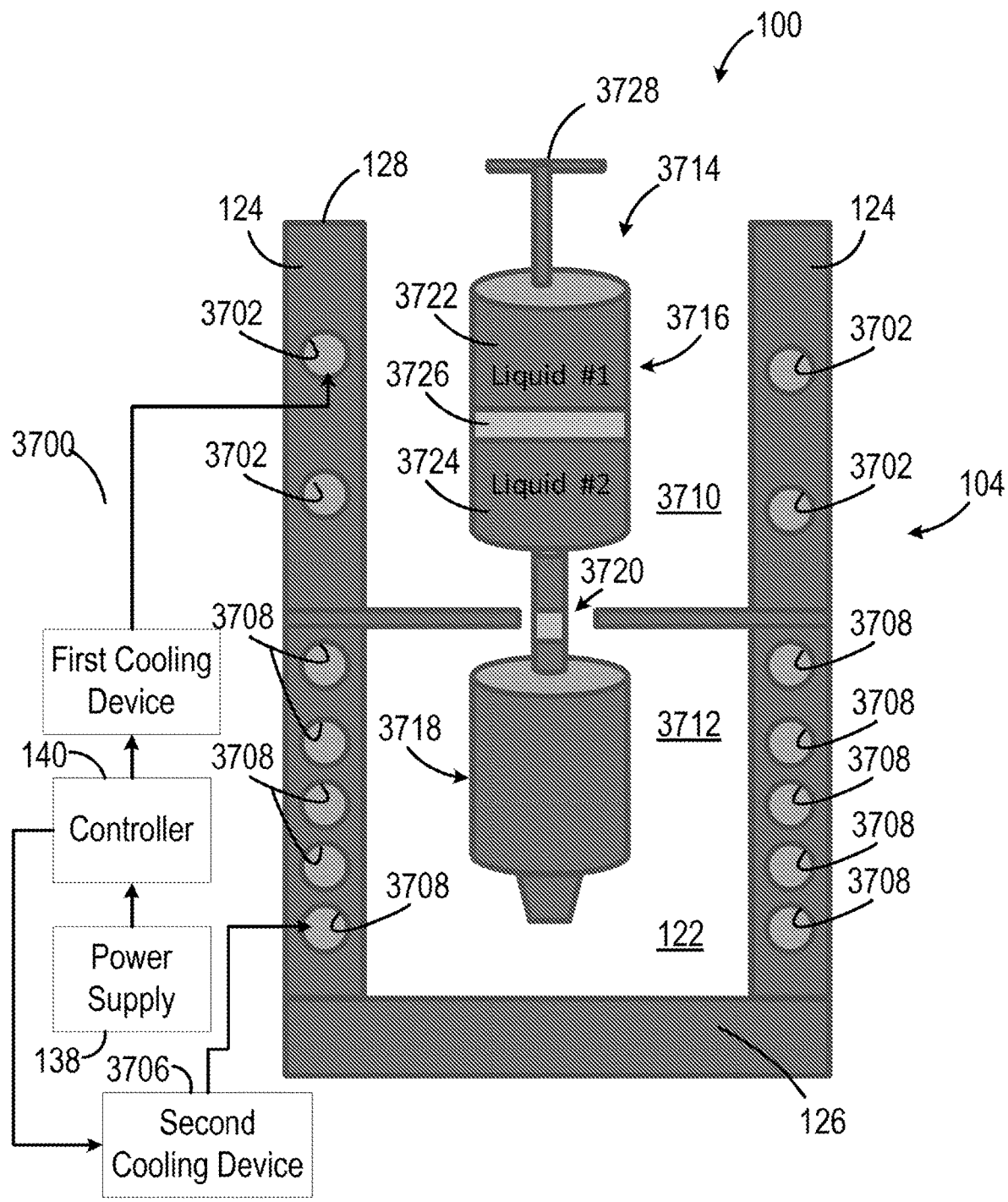
FIG. 40 is a schematic illustration of a medical ice slurry production system according to yet another non-limiting example of the present disclosure.

FIG. 40 illustrates another non-limiting example of the medical ice slurry production system 100. The medical ice slurry production system 100 of FIG. 40 is similar to the medical ice slurry production systems 100 of FIGS. 1 and 20 except as described below or is apparent from the figures. Like components are identified with similar reference numerals. As shown in FIG. 40, the medical ice slurry production system 100 includes a first cooling passage 3702 coupled to a first cooling device 3700 and a second cooling passage 3706 coupled to a second cooling device 3706. The first cooling passage 3702 is arranged within the sides 124 of the housing to provide cooling to a first cavity 3710 arranged within the housing 104. The second cooling passage 3708 is arranged within the sides 124 of the housing 104 to provide cooling to a second cavity 3712 arranged within the housing 104.

The medical ice slurry production system 100 includes a disposable cartridge 3714. The disposable cartridge 3714 includes a first syringe chamber 3716, a second syringe chamber 3718, and a microdroplet device 3720 arranged between the first syringe chamber 3716 and the second syringe chamber 3718. When placed in the housing 104, the first syringe chamber 3716 is arranged within the first cavity 3710, and the second syringe chamber 3718 is arranged within the second cavity 3718. The first syringe chamber 3716 is pre-filled with a sterile first liquid 3722, a sterile second liquid 3724, and a collapsible separator 3726 arranged between the first liquid 3722 and the second liquid 3724. The second liquid 3724 is arranged adjacent to the microdroplet device 3720. A plunger 3728 is slidably received within the first syringe chamber 3716 and configured to inject the first liquid 3722 and thereby the second liquid 3724 (liquids are substantially incompressible) towards the second syringe chamber 3718.

In operation, the controller 140 controls the first cooling device 3700 to maintain the first cavity 3710 at a cool temperature (e.g., approximately 2° C.) and controls the second cooling device 3706 to maintain the second cavity 3712 at a temperature substantially below freezing (e.g., −100° C.). Once the desired temperatures are achieved in the first and second cavities 3710 and 3712, the plunger 3728 is displaced to inject the second liquid 3724 through the microdroplet device 3720 and into the second chamber 3718. The microdroplet device 3720 and the freezing temperature of the second cavity 3712 enable the formation of ice crystals of a desired size (controlled by the microdroplet device 3720) in the second syringe cavity 3718. Next, the collapsible separator 3726 is crushed, or displaced, to enable the first liquid 3722 to fall into the second syringe chamber 3718 thereby suspending the previously formed ice crystals in the first liquid 3722 (i.e., producing a sterile slurry composition at a desired temperature with ice crystals of a desired size). The sterile slurry mixture formed is then able to be injected into a patient.

FIG. 41 illustrates one non-limiting example of the medical ice slurry production system 100. The medical ice slurry production system 100 of FIG. 41 is similar to the medical ice slurry production systems 100 of FIG. 40 except as described below or is apparent from the figures. Like components are identified with similar reference numerals. As illustrated in FIG. 41, the first syringe chamber 3716 includes an ice tray 3800 arranged therein, and the second syringe chamber 3718 is pre-filled with a first liquid 3802. The ice tray 3800 can be fabricated from a flexible material. As illustrated in FIG. 42, the ice tray 3800 defines a plurality of ice cavities 3900 each pre-filled with liquid 3902 and dimensioned to form an ice crystal of a desired size and shape.

In operation, the controller 140 controls the first cooling device 3700 to maintain the first cavity 3710 at a freezing temperature (e.g., approximately −20° C.) and controls the second cooling device 3706 to maintain the second cavity 3712 at a warmer temperature (e.g., 2° C.). Once the desired temperatures are achieved in the first and second cavities 3710 and 3712 and the ice crystals have formed in the ice tray 3800, the ice tray 3800 is inverted (FIG. 42) to release the formed ice crystals 3902 from their respective ice cavities 3900. When released, the ice crystals 3902 fall into the second syringe chamber 3718 thereby suspending the previously formed ice crystals in the first liquid 3802 (i.e., producing a sterile slurry composition at a desired temperature with ice crystals of a desired size). The sterile slurry mixture formed is then able to be agitated, if desired, and injected into a patient. In certain embodiments, the first liquid 3802 can include saline, lactated ringers, or a solution to make an emulsion, which is generally a fine dispersion of insoluble droplets or p articles.

In each of the embodiments discussed above, it should also be appreciated that the temperature inside the medical ice slurry mixing chamber, (e.g., any of the canisters or disposable cartridges described herein) can be equilibrated with any one or more of the cooling devices, liquids or gases discussed herein so as to provide a uniformly cooled medical ice slurry. For example, referring to the systems of FIGS. 1-3, these systems can be configured such that the temperature inside the cartridge 102 equilibrates with the cooling liquid or gas in the passageways or coils 136, or the cooling liquid or gas in cavity 122.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A medical ice slurry production system comprising:
    a sealed disposable cartridge holding a non-frozen, sterile medical slurry composition, such that the sterile medical slurry composition is self-contained within a closed environment;
    a housing supporting the sealed disposable cartridge, the housing including an actuator and defining an internal cavity dimensioned to receive the sealed disposable cartridge;
    a cooling device operable with the housing to cool the non-frozen slurry composition held in the sealed disposable cartridge, while placed in the housing, to a temperature sufficient to form ice crystals in the medical slurry composition inside the sealed disposable cartridge;
    an agitator operable with the actuator of the housing to agitate the medical slurry composition such that the ice crystals are reduced to a size sufficient to allow the medical slurry composition including the reduced ice crystals to be delivered to a patient through an end of a needle; and
    an access port structured and arranged to allow the medical slurry composition including the reduced ice crystals to be withdrawn or injected from the sealed disposable cartridge, while maintaining the sterility of the medical slurry composition including the reduced ice crystals;
    wherein the access port is defined in the sealed disposable cartridge; and
    wherein the sealed disposable cartridge is configured to be removably placed in the housing.

2. The medical ice slurry production system of claim 1, wherein the sealed disposable cartridge includes one of a syringe or a canister.

3. The medical ice slurry production system of claim 1, wherein the access port is structured and arranged to allow a syringe to engage the access port and withdraw the slurry composition.

4. The medical ice slurry production system of claim 1, wherein the actuator includes at least one of a vibrating device or a rotating device.

5. The medical ice slurry production system of claim 1, wherein the agitator includes a rotating device structured and arranged to rotate back and forth.

6. The medical ice slurry production system of claim 1, wherein the agitator is attached to the sealed disposable cartridge.

7. The medical ice slurry production system of claim 1, wherein the agitator is attached to the actuator supported by the housing.

8. The medical ice slurry production system of claim 1, wherein the actuator includes a motor structured and arranged to cause the agitator to agitate the medical slurry composition inside the sealed disposable cartridge such that ice crystals inside the sealed disposable cartridge are reduced to a size sufficient to allow the medical slurry composition including the reduced ice crystals to be delivered through an end of a needle for injecting the medical slurry composition into a patient.

9. The medical ice slurry production system of claim 1, wherein the access port is a first access port defined in the sealed disposable cartridge, and which includes a second access port defined in the housing, the first access port and the second access port in fluid communication so as to allow the medical ice slurry composition to be withdrawn from the sealed disposable cartridge while maintaining the sterility of the medical slurry composition.

10. The medical ice slurry production system of claim 1, wherein the cooling device includes at least one of standard refrigeration, magnetic refrigeration, electrical cooling, or chemical cooling.

11. The medical ice slurry production system of claim 1, wherein at least one of (i) a luer lock with a shut-off, (ii) a pressure valve, (iii) a quick disconnect, (iv) a one-way valve with luer lock, and (v) a sterile rubber stopper is operable with the access port to selectively allow the sterile medical slurry composition to be withdrawn from the sealed disposable cartridge through the access port.

12. The medical ice slurry production system of claim 1, wherein the reduced ice crystals are less than approximately one millimeter.

13. The medical ice slurry production system of claim 1, wherein the actuator is operable to rotate the agitator at a rotational speed between approximately 1000 revolutions per minute and 45000 revolutions per minute.

14. The medical ice slurry production system of claim 1, wherein the agitator includes one or more blades each sized to define a length between approximately 12.5% and approximately 99% of a diameter of the sealed disposable cartridge.

15. The medical ice slurry production system of claim 1, further comprising:
    a pump operable to pump the medical slurry composition including the reduced ice crystals out of the access port of the sealed disposable cartridge through a disposable delivery tube, while maintaining the sterility of the medical slurry composition including the reduced ice crystals.

16. The medical ice slurry production system of claim 1, wherein the housing defines a passageway configured to receive a cooling liquid or gas provided by the cooling device.

17. A method for producing a medical ice slurry, the method comprising:

placing a sealed disposable cartridge holding a non-frozen, sterile medical slurry composition in a housing; the housing including an actuator and defining an internal cavity dimensioned to receive the sealed disposable cartridge such that the sterile medical slurry composition is self-contained within a closed environment;

while the sealed disposable cartridge is placed in the housing, cooling, using a cooling device operable with the housing, the sealed disposable cartridge to a temperature sufficient to form ice crystals in the medical slurry composition inside the sealed disposable cartridge; and agitating, using an agitator operable with the actuator of the housing, the medical slurry composition held in the sealed disposable cartridge such that the ice crystals inside the sealed disposable cartridge are reduced to a size sufficient to allow the medical slurry composition including the reduced ice crystals to be delivered to a patient through an end of a needle through an access port defined in the sealed disposable cartridge;

wherein the access port is structured and arranged to allow the medical slurry composition including the reduced ice crystals to be withdrawn or injected from the sealed disposable cartridge, while maintaining the sterility of the medical slurry composition including the reduced ice crystals.

18. The method of claim 17, which includes withdrawing the medical slurry composition including the reduced ice crystals from the sealed disposable cartridge while maintaining the sterility of the medical slurry composition.

19. The method of claim 17, which includes pumping the medical slurry composition including the reduced ice crystals from the sealed disposable cartridge while maintaining the sterility of the medical slurry composition.

20. The method of claim 17, wherein agitating includes causing an actuator to agitate the medical slurry composition such that the ice crystals inside the sealed disposable cartridge are reduced to a size sufficient to allow the medical slurry composition including the reduced ice crystals to be delivered to a patient through an end of a needle.

* * * * *